(12) United States Patent
Miracle et al.

(10) Patent No.: US 7,018,978 B2
(45) Date of Patent: *Mar. 28, 2006

(54) FRAGRANCE PRO-ACCORDS AND ALDEHYDE AND KETONE FRAGRANCE LIBRARIES

(75) Inventors: Gregory Scot Miracle, Hamilton, OH (US); Kenneth Nathan Price, Wyoming, OH (US)

(73) Assignee: Procter & Gamble Company, Cincinnati, OH (US)

( * ) Notice: Subject to any disclaimer, the term of this patent is extended or adjusted under 35 U.S.C. 154(b) by 350 days.

This patent is subject to a terminal disclaimer.

(21) Appl. No.: 10/417,071

(22) Filed: Apr. 16, 2003

(65) Prior Publication Data

US 2003/0207786 A1     Nov. 6, 2003

Related U.S. Application Data

(63) Continuation of application No. 09/804,100, filed on Mar. 12, 2001, now abandoned, which is a continuation of application No. PCT/US99/24823, filed on Oct. 22, 1999.

(60) Provisional application No. 60/105,380, filed on Oct. 23, 1998.

(51) Int. Cl.
*A61K 7/46* (2006.01)

(52) U.S. Cl. .................. 512/2; 512/8; 512/12; 512/22; 512/24; 512/25; 564/454; 568/591

(58) Field of Classification Search ............... 512/25, 512/12, 8, 22, 24, 2; 564/454; 568/591
See application file for complete search history.

(56) References Cited

U.S. PATENT DOCUMENTS

| | | | |
|---|---|---|---|
| 2,960,433 A | 11/1960 | Eden | |
| 3,821,421 A | 6/1974 | Begemann et al. | |
| 4,011,233 A | 3/1977 | Dubs et al. | |
| 4,129,569 A | 12/1978 | Schreiber et al. | |
| 6,103,678 A | 8/2000 | Masschelein et al. | |
| 6,551,987 B1 | 4/2003 | Miracle et al. | |
| 6,861,402 B1 * | 3/2005 | Miracle et al. | 512/2 |

FOREIGN PATENT DOCUMENTS

| | | |
|---|---|---|
| DE | 2338516 A1 | 7/1973 |
| EP | 0 841 391 A1 | 6/1997 |
| WO | WO 97/34986 A1 | 9/1997 |
| WO | WO 98/20102 A1 | 5/1998 |
| WO | WO 00/63329 A1 | 10/2000 |
| WO | WO 00/72816 A1 | 12/2000 |

OTHER PUBLICATIONS

Schmolka, Irving R., "Thiazolidine Chemistry. II." The Preparation of 2-Substituted Thiazolidine-4-carboxylic Acids, Journal of Organic Chemistry, vol. 22, No. 8, Aug. 14, 1957, pp 943-946, XP-002138074.

Taylor, WG et al, "Synthesis and mosquito repellent properties of 2,2-dialkyl- and 2-alkyl-4,4-dimethyl-N-actyloxazolidines" Pesticide Science, vol. 46, No. 4, (Apr. 1996) pp 307-314, XP002138075.

Soloway H. et al., "2-Substituted-thiazolidine-carboxylic acids", Journal of the American Chemical Society, vol. 70, No. 4, Apr. 1948, pp 1667-1668, XP002138076.

Database Crossfire 'Online!, Beilstein Institut fuer Literatur der organischen Chemie, XP002138077, Beilstein Registry No. 14509, 84441 and 87029 & Justus Liebigs Ann. Chem., vol. 614, 1958, p 149., 154-156.

Database Crossfire 'Online!, Beilstein Institut fuer Literatur der organischen Chemie, XP002138078, Beilstein Registry Nos. 5502280 and 5498160 & Chem. Lett., 1987, pp 1511-1512.

Database Crossfire 'Online!, Beilstein Institut fuer Literatur der organischen Chemie, XP002138079, Beilstein Registry No. 1074375 & Chem. Pharm. Bull., vol. 13, No. 10, 1965, pp 1151-1159.

Database Crossfire 'Online!, Beilstein Institut fuer Literatur der organischen Chemie, XP002138080, Beilstein Registry No. 751979 & Yakugaku Zasshi, vol. 84, 1964, p 183-187.

Database Crossfire 'Online!, Beilstein Institut fuer Literatur der organischen Chemie, XP002138081, Beilstein Registry No. 970477 & J. Heterocycl. Chem., No. 3, 1966, pp 531-532.

(Continued)

*Primary Examiner*—Monique T. Cole
(74) *Attorney, Agent, or Firm*—James F. McBride; Kim W. Zerby; Steve. W. Miller

(57) ABSTRACT

The present invention relates to novel heterocyclic pro-fragrances, preferably oxazolidines, tertahydro-1,3-oxazines, thiazolidines, or tetrahydro-1,3-thiazines, more preferably oxazolidines, or tertahydro-1,3-oxazines, most preferably oxazolidines, which are capable of sustained release of fragrance raw material ketones and aldehydes and to fragrance delivery systems which comprise said pro-fragrances.

10 Claims, No Drawings

OTHER PUBLICATIONS

Database Crossfire 'Online!, Beilstein Institut fuer Literatur der organischen Chemie, XP002138082, Beilstein Registry No. 4449416 & Tetrahedron Lett., vol. 26, No. 43, 1985, pp 5303-5306.

Database Crossfire 'Online!, Beilstein Institut fuer Literatur der organischen Chemie, XP002138083, Beilstein Registry No. 5062528 & Tetrahedron, vol. 44, No. 11, 1988, pp 3107-3118.

Database Crossfire 'Online!, Beilstein Institut fuer Literatur der organischen Chemie, XP00213084, Beilstein Registry No. 7976083 & Tetrahedron Lett., vol. 39, No. 16, 1998, pp 2327-2330.

Database Crossfire 'Online!, Beilstein Institut fuer Literatur der organischen Chemie, XP002138085, Beilstein Registry No. 4372280, 4378144 and 4371875 & J. Org. Chem. USSR, vol. 16, 1980, pp 2163-2168.

* cited by examiner

FRAGRANCE PRO-ACCORDS AND ALDEHYDE AND KETONE FRAGRANCE LIBRARIES

CROSS REFERENCE TO RELATED APPLICATIONS

This application is a continuation and claims priority under 35 U.S.C. §120 to U.S. application Ser. No. 09/804,100, filed Mar. 12, 2001 now abandoned, which in turn is a continuation under 35 U.S.C. §120 of, PCT International Application Ser. No. PCT/US99/24823 filed Oct. 22, 1999, which claims priority to U.S. Provisional Application Ser. No. 60/105,380, filed Oct. 23, 1998, (now abandoned).

FIELD OF THE INVENTION

The present invention relates to novel fragrance pro-accords which release fragrance raw material aldehydes and ketones suitable for use in perfume and fine fragrance compositions thereby providing said compositions with enduring fragrance characteristics. The present invention further relates to a fragrance delivery system which comprises the novel fragrance pro-accords of the present invention in combination with a) one or more pro-accords inter alia acetals, ketals, orthoesters, orthocarbonates, and b) one or more fragrance raw materials.

BACKGROUND OF THE INVENTION

Humans have applied scents and fragrances to their skin since antiquity. Originally these aesthetically pleasing materials were commonly isolated in raw form as resins, gums or essential oils from natural sources, inter alia, the bark, roots, leaves and fruit of indigenous plants. These resins, gums, and oils were directly applied to the body or diluted with water or other solvent, including in some cases, wine. With the advent of modern chemistry, individual components responsible for the odor properties of these resins, gums and oils were isolated and subsequently characterized. Aside from common "perfume vehicles" inter alia, fine perfumes, colognes, eau de toilettes, and after-shave lotions, a wide variety of personal care or personal hygiene items also deliver for aesthetic reasons fragrance notes, accords, or fragrance "characteristics".

It is well known that mixtures of perfume or fragrance raw materials when deposited on the skin lose intensity and may change character with time, mainly due to factors such as differential evaporation and skin penetration. Many attempts have been made to minimize these drawbacks, but so far without notable success. Particularly, efforts have been made to prolong the diffusion, as well as to improve other characteristics of fragrance materials, by e.g. increasing the fragrance raw material concentration or by using additives such as silicones, glycerol, polyethylene glycols and so on. Such additions, however, have never been adequate to increase the longevity of the fragrance odor.

In addition to alcohols and esters, aldehydes and ketones form the most commonly delivered fragrance raw materials. Alcohols and esters can be suitably released in a delayed manner from an orthoester pro-accord or pro-fragrance. The controllable release of these fragrance raw materials thus provides the formulator with a means for delivering these fragrance ingredients, not only as an accord, but in a delayed-releasable manner over a period of time fragrance which is desirable to the fine fragrance and perfume user. However, the primary means for delivering aldehydes and ketones in a time-releasable manner has typically been the acetal and ketal pro-fragrance. Notwithstanding the fact that these materials are capable of delivering the required aldehyde and ketone under the proper acidic conditions, in the past, because there was no means of adjusting the release profiles of pro-fragrances, these compounds have not provided the formulator with a highly controllable method for sustained and predictable delivery of aldehydes and ketones.

Accordingly, there remains a need in the art for a pro-accord which can be formulated into fine fragrances, perfumes, personal care and personal hygiene products wherein aldehyde and ketone fragrance raw material components can be released in a highly controllable manner to provide enhanced fragrance longevity.

SUMMARY OF THE INVENTION

The present invention meets the aforementioned needs in that it has been surprisingly discovered that aldehyde and ketone fragrance raw materials can be controllably released from novel heterocyclic pro-accords or pro-fragrances. The novel pro-fragrances or pro-accords of the present invention are heterocycles, preferably oxazolidines, tertahydro-1,3-oxazines, thiazolidines, or tetrahydro-1,3-thiazines, more preferably oxazolidines, or tertahydro-1,3-oxazines, most preferably oxazolidines. These pro-fragrances provide controllable release of fragrance raw materials and thereby enhance the longevity of perfumes and fragrances when applied to human skin. The pro-accords or pro-fragrances of the present invention can be easily formulated into any type of personal care or personal hygiene articles inter alia fine fragrances, perfumes, deodorants, body lotions or creams, ointments, balms, salves, antiseptics, suntan lotions, or shampoos.

The pro-fragrances and/or pro-accords described herein comprise fragrance raw materials in a stable, releasable "pro-fragrance" form. In general, the pro-fragrances can be formulated into any product which is deliverable to human skin, directly or indirectly, provided the product pH, carriers and adjunct materials are compatible with the pro-fragrance chemical form. Once in contact with human skin, the heterocyclic pro-fragrance releases a fragrance raw material at a rate which provides extended fragrance benefits. The fragrance delivery systems of the present invention can be a mixture of any number of pro-fragrances or pro-accords and can cover any fragrance "characteristic" or desired fragrance volatility.

The first aspect of the present invention relates to a pro-fragrance or pro-accord having the formula:

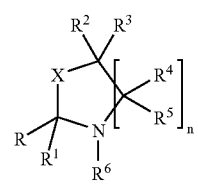

wherein said pro-fragrance or pro-accord releases an aldehyde or a ketone fragrance raw material, wherein X is oxygen or sulfur; R is:
 a) $C_6$–$C_{22}$ substituted or unsubstituted linear alkyl;
 b) $C_6$–$C_{22}$ substituted or unsubstituted branched alkyl;
 c) $C_6$–$C_{22}$ substituted or unsubstituted linear alkenyl;
 d) $C_6$–$C_{22}$ substituted or unsubstituted branched alkenyl;

e) $C_6$–$C_{22}$ substituted or unsubstituted cycloalkyl;
f) $C_6$–$C_{22}$ substituted or unsubstituted branched cycloalkyl;
g) $C_6$–$C_{22}$ substituted or unsubstituted cycloalkenyl;
h) $C_6$–$C_{22}$ substituted or unsubstituted branched cycloalkenyl;
i) $C_6$–$C_{22}$ substituted or unsubstituted aryl;
j) $C_6$–$C_{22}$ substituted or unsubstituted heterocyclicalkyl;
k) $C_6$–$C_{22}$ substituted or unsubstituted heterocyclicalkenyl;
l) and mixtures thereof;

$R^1$ is:
a) hydrogen;
b) $C_1$–$C_{10}$ substituted or unsubstituted linear alkyl;
c) $C_3$–$C_{10}$ substituted or unsubstituted branched alkyl;
d) $C_2$–$C_{10}$ substituted or unsubstituted linear alkenyl;
e) $C_3$–$C_{10}$ substituted or unsubstituted branched alkenyl;
f) $C_3$–$C_{15}$ substituted or unsubstituted cycloalkyl;
g) $C_4$–$C_{15}$ substituted or unsubstituted branched cycloalkyl;
h) $C_4$–$C_{15}$ substituted or unsubstituted cycloalkenyl;
i) $C_5$–$C_{15}$ substituted or unsubstituted branched cycloalkenyl;
j) $C_6$–$C_{15}$ substituted or unsubstituted aryl;
k) $C_6$–$C_{22}$ substituted or unsubstituted heterocyclicalkyl;
l) $C_6$–$C_{22}$ substituted or unsubstituted heterocyclicalkenyl;
m) and mixtures thereof;

R and $R^1$ can be taken together to form a substituted or unsubstituted ring having in the ring from 3 to 10 carbon atoms;

each $R^2$, $R^3$, and each $R^4$ and $R^5$ pair are independently:
a) $R^1$;
b) hydroxyl;
c) a carbonyl comprising unit having the formula:

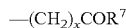

wherein $R^7$ is:
i) —OH;
ii) —$OR^8$ wherein $R^8$ is hydrogen, $C_1$–$C_{15}$ substituted or unsubstituted linear alkyl, $C_1$–$C_{15}$ substituted or unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen;
iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
iv) $C_1$–$C_{22}$ substituted or unsubstituted linear alkyl;
v) $C_1$–$C_{22}$ substituted or unsubstituted branched alkyl;
vi) $C_2$–$C_{22}$ substituted or unsubstituted linear alkenyl;
vii) $C_3$–$C_{22}$ substituted or unsubstituted branched alkenyl;
viii) $C_3$–$C_{22}$ substituted or unsubstituted cycloalkyl;
ix) $C_6$–$C_{22}$ substituted or unsubstituted aryl;
x) $C_6$–$C_{22}$ substituted or unsubstituted heterocyclicalkyl;
xi) $C_6$–$C_{22}$ substituted or unsubstituted heterocyclicalkenyl;
the index x is from 1 to 22;
d) alkyleneoxy units having the formula:

—$(CR^{10}R^{11})_y(CHR^{12}CHR^{13}O)_zR^{14}$ wherein each $R^{10}$, $R^{11}$, and $R^{12}$ is independently;
i) hydrogen;
ii) —OH;
iii) $C_1$–$C_4$ alkyl;
iv) or mixtures thereof;
$R^{13}$ is:
i) hydrogen;
ii) $C_1$–$C_4$ alkyl;
iii) or mixtures thereof;
$R^{14}$ is:
i) hydrogen;
ii) $C_1$–$C_4$ alkyl;
iii) or mixtures thereof;
$R^{10}$ and $R^{11}$ can be taken together to form a $C_3$–$C_6$ spiroannulated ring, carbonyl unit, or mixtures thereof; y has the value from 0 to 10, z has the value from 1 to 50;
e) and mixtures thereof;

$R^6$ is:
a) $C_1$–$C_{10}$ substituted linear alkyl;
b) $C_3$–$C_{10}$ substituted branched alkyl;
c) $C_2$–$C_{10}$ substituted or unsubstituted linear alkenyl;
d) $C_3$–$C_{10}$ substituted or unsubstituted branched alkenyl;
e) $C_3$–$C_{15}$ substituted cycloalkyl;
f) $C_4$–$C_{15}$ substituted or unsubstituted branched cycloalkyl;
g) $C_4$–$C_{15}$ substituted or unsubstituted cycloalkenyl;
h) $C_5$–$C_{15}$ substituted or unsubstituted branched cycloalkenyl;
i) $C_6$–$C_{15}$ substituted aryl;
j) $C_6$–$C_{22}$ substituted or unsubstituted heterocyclicalkyl;
k) $C_6$–$C_{22}$ substituted or unsubstituted heterocyclicalkenyl;
l) a carbonyl comprising unit having the formula:

—$(CH_2)_xCOR^7$ wherein $R^7$ is:
i) —OH;
ii) —$OR^8$ wherein $R^8$ is hydrogen, $C_1$–$C_{15}$ substituted linear alkyl, $C_{11}$–$C_{15}$ unsubstituted linear alkyl, $C_1$–$C_{15}$ substituted branched alkyl, $C_{11}$–$C_{15}$ unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen or thioalkyl;
iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
iv) $C_1$–$C_{22}$ substituted or unsubstituted linear alkyl;
v) $C_1$–$C_{22}$ substituted or unsubstituted branched alkyl;
vi) $C_2$–$C_{22}$ substituted or unsubstituted linear alkenyl;
vii) $C_3$–$C_{22}$ substituted or unsubstituted branched alkenyl;
viii) $C_3$–$C_{22}$ substituted or unsubstituted cycloalkyl;
ix) $C_6$–$C_{22}$ substituted or unsubstituted aryl;
x) $C_6$–$C_{22}$ substituted or unsubstituted heterocyclicalkyl;
xi) $C_6$–$C_{22}$ substituted or unsubstituted heterocyclicalkenyl;
the index x is from 0 to 22;
m) alkyleneoxy units having the formula:

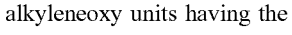

wherein each $R^{10}$, $R^{11}$, and $R^{12}$ is independently;
i) hydrogen;
ii) —OH;
iii) $C_1$–$C_4$ alkyl;
iv) or mixtures thereof;

$R^{13}$ is:
i) hydrogen;
ii) $C_1$–$C_4$ alkyl;
iii) or mixtures thereof;
$R^{14}$ is:
i) hydrogen;
ii) $C_1$–$C_4$ alkyl;
iii) or mixtures thereof;
$R^{10}$ and $R^{11}$ can be taken together to form a $C_3$–$C_6$ spiroannulated ring, carbonyl unit, or mixtures thereof; y has the value from 0 to 10, z has the value from 1 to 50;
n) and mixtures thereof;
any two $R^2$, $R^3$, $R^4$, $R^5$, or $R^6$ units can be taken together to form:
i) a carbonyl moiety;
ii) a $C_3$–$C_6$ spiroannulated ring;
iii) a heterocyclic aromatic ring comprising from 5 to 7 atoms;
iv) a non-heterocyclic aromatic ring comprising from 5 to 7 atoms;
v) a heterocyclic ring comprising from 5 to 7 atoms;
vi) a non-heterocyclic ring comprising from 5 to 7 atoms;
vii) or mixtures thereof; and
the index n is an integer from 1 to 3.

A second aspect of the present invention relates to fragrance delivery systems which comprise a pro-fragrance or pro-accord having the formula:

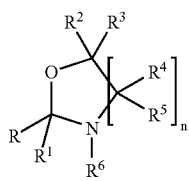

wherein said pro-fragrance or pro-accord releases an aldehyde or a ketone fragrance raw material, wherein X is oxygen or sulfur; R is:
a) $C_6$–$C_{22}$ substituted or unsubstituted linear alkyl;
b) $C_6$–$C_{22}$ substituted or unsubstituted branched alkyl;
c) $C_6$–$C_{22}$ substituted or unsubstituted linear alkenyl;
d) $C_6$–$C_{22}$ substituted or unsubstituted branched alkenyl;
e) $C_6$–$C_{22}$ substituted or unsubstituted cycloalkyl;
f) $C_6$–$C_{22}$ substituted or unsubstituted branched cycloalkyl;
g) $C_6$–$C_{22}$ substituted or unsubstituted cycloalkenyl;
h) $C_6$–$C_{22}$ substituted or unsubstituted branched cycloalkenyl;
i) $C_6$–$C_{22}$ substituted or unsubstituted aryl;
j) $C_6$–$C_{22}$ substituted or unsubstituted heterocyclicalkyl;
k) $C_6$–$C_{22}$ substituted or unsubstituted heterocyclicalkenyl;
l) and mixtures thereof;
$R^1$ is:
a) hydrogen;
b) $C_1$–$C_{10}$ substituted or unsubstituted linear alkyl;
c) $C_3$–$C_{10}$ substituted or unsubstituted branched alkyl;
d) $C_2$–$C_{10}$ substituted or unsubstituted linear alkenyl;
e) $C_3$–$C_{10}$ substituted or unsubstituted branched alkenyl;
f) $C_3$–$C_{15}$ substituted or unsubstituted cycloalkyl;
g) $C_4$–$C_{15}$ substituted or unsubstituted branched cycloalkyl;
h) $C_4$–$C_{15}$ substituted or unsubstituted cycloalkenyl;
i) $C_5$–$C_{15}$ substituted or unsubstituted branched cycloalkenyl;
j) $C_6$–$C_{15}$ substituted or unsubstituted aryl;
k) $C_6$–$C_{22}$ substituted or unsubstituted heterocyclicalkyl;
l) $C_6$–$C_{22}$ substituted or unsubstituted heterocyclicalkenyl;
R and $R^1$ can be taken together to form a substituted or unsubstituted ring having in the ring from 3 to 10 carbon atoms; and
each $R^2$, $R^3$, $R^6$ and each $R^4$ and $R^5$ pair are independently:
a) $R^1$;
b) hydroxyl;
c) a carbonyl comprising unit having the formula:

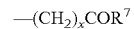

wherein $R^7$ is:
i) —OH;
ii) —$OR^8$ wherein $R^8$ is hydrogen, $C_1$–$C_{15}$ substituted or unsubstituted linear alkyl, $C_1$–$C_{15}$ substituted or unsubstituted branched alkyl, $C_2$–$C_{22}$ substituted or unsubstituted linear alkenyl, $C_3$–$C_{22}$ substituted or unsubstituted branched alkenyl, or mixtures thereof;
iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
iv) $C_1$–$C_{22}$ substituted or unsubstituted linear alkyl;
v) $C_1$–$C_{22}$ substituted or unsubstituted branched alkyl;
vi) $C_2$–$C_{22}$ substituted or unsubstituted linear alkenyl;
vii) $C_3$–$C_{22}$ substituted or unsubstituted branched alkenyl;
viii) $C_3$–$C_{22}$ substituted or unsubstituted cycloalkyl;
ix) $C_6$–$C_{22}$ substituted or unsubstituted aryl;
x) $C_6$–$C_{22}$ substituted or unsubstituted heterocyclicalkyl;
xi) $C_6$–$C_{22}$ substituted or unsubstituted heterocyclicalkenyl;
the index x is from 0 to 22;
d) alkyleneoxy units having the formula:

wherein each $R^{10}$, $R^{11}$, and $R^{12}$ is independently;
i) hydrogen;
ii) —OH;
iii) $C_1$–$C_4$ alkyl;
iv) or mixtures thereof;
$R^{13}$ is:
i) hydrogen;
ii) $C_1$–$C_4$ alkyl;
iii) or mixtures thereof;
$R^{14}$ is:
i) hydrogen;
ii) $C_1$–$C_4$ alkyl;
iii) or mixtures thereof;
$R^{10}$ and $R^{11}$ can be taken together to form a $C_3$–$C_6$ spiroannulated ring, carbonyl unit, or mixtures thereof; y has the value from 0 to 10, z has the value from 1 to 50;
e) any two $R^2$, $R^3$, $R^4$, $R^5$, or $R^6$ units can be taken together to form:
i) a carbonyl moiety;
ii) a $C_3$–$C_6$ spiroannulated ring;
iii) a heterocyclic aromatic ring comprising from 5 to 7 atoms;
iv) a non-heterocyclic aromatic ring comprising from 5 to 7 atoms;

v) a heterocyclic ring comprising from 5 to 7 atoms;
vi) a non-heterocyclic ring comprising from 5 to 7 atoms;
vii) or mixtures thereof;
f) and mixtures thereof; and
the index n is an integer from 1 to 3.

The fragrance delivery systems of the present invention which comprise a heterocyclic pro-fragrance or pro-accord comprise:
A) from about 1%, preferably from about 10%, more preferably from about 25% to about 100%, preferably to about 90%, more preferably to about 75%, most preferably to about 50% by weight, of a pro-fragrance and/or pro-accord component; and
B) optionally from about 1%, preferably from about 25% to about 99%, preferably to about 90%, more preferably to about 75%, most preferably to about 50% by weight, of a fragrance raw material component.

The present invention further relates to a method for providing an sustained duration aesthetic perfume or fragrance benefit comprising the step of contacting a surface with a composition which comprises the fragrance delivery system of the present invention.

The present invention further relates to pro-fragrance libraries which are formed from an admixture of two or more fragrance raw materials and which use the same heterocyclic ring to provide a releasable admixture of fragrance ingredients suitable for use in the fragrance delivery systems of the present invention.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to pro-fragrances and/or pro-accords which release an aldehyde or ketone fragrance raw material. The present invention further relates to fragrance delivery systems which comprise one or more of the herein described pro-fragrances.

Key to the pro-fragrances and/or pro-accords of the present invention is the ability of the formulator to prepare a compound (pro-fragrance or pro-accord) which has a specific release rate of aldehyde or ketone. The formulator may design pro-fragrances or pro-accords to release at any rate which the formulator finds useful to the consumer. In addition, by determining the Fragrance Release Half-life of each particular pro-fragrance, the formulator is able to make a side by side comparison of structurally dissimilar molecules and evaluate their relative fragrance raw material release patterns. In this way not only can the formulator determine with minimal experimentation whether a compound is suitable for use as a pro-fragrance, but also determine the release profile of the molecule. Therefore, a slight structural modification can result in a more finely tuned fragrance delivery system.

Mixtures of fragrance materials are known by those skilled in the art of fragrances and perfumes as "accords". The term "accord" as used herein is defined as "a mixture of two or more 'fragrance raw materials' which are artfully combined to impart a pleasurable scent, odor, essence, or fragrance characteristic". For the purposes of the present invention "fragrance raw materials" are herein defined as compounds having a molecular weight of at least 100 g/mol and which are useful in imparting an odor, fragrance, essence, or scent either alone or in combination with other "fragrance raw materials".

The fragrance delivery systems of the present invention comprise one or more of the herein described pro-fragrances or pro-accords. In its broadest form, the fragrance delivery system comprises:
A) from about 1%, preferably from about 10%, more preferably from about 25% to about 100%, preferably to about 90%, more preferably to about 75%, most preferably to about 50% by weight, of a cyclic pro-fragrance or pro-accord component as described herein below; and
B) optionally from about 1%, preferably from about 25% to about 99%, preferably to about 90%, more preferably to about 75%, most preferably to about 50% by weight, of a fragrance raw material component.

The fragrance delivery system of the present invention is therefore an admixture of pro-fragrances/pro-accords and optionally other fragrance raw materials with provides a sustained and enhanced delivery of fragrance or other aesthetic perfume benefit to the user. The fragrance delivery system of the present invention can be used in any composition which intends to provide an aesthetic benefit inter alia fine fragrances, perfumes, personal care products, deodorants, shampoos, laundry detergents, malodor masking agents.

Aesthetic perfume or fragrance raw material delivery systems typically comprise components which react with human olfactory sites resulting in what is known as a "fragrance". Typical molecules which comprise perfume fragrances are linear and cyclic alkenes (i.e., terpenes), primary, secondary and tertiary alcohols, nitriles, ethers, saturated and unsaturated aldehydes, esters, ketones, and mixtures thereof. Each of these perfume fragrances can be classified according to its volatility into one of three categories; "top note", "middle note", and "base note".

For the purposes of the present invention "top note" fragrances are defined as "fragrances having a high vapor pressure, and when applied to a paper sachet, vaporization takes place within 2 hours, and no scent remains; essentially, the initial impression of the perfume formulation is provided by top notes".

For the purposes of the present invention "middle note" fragrances are defined as "fragrances having a medium vapor pressure, and when applied to a paper sachet, the scent remains from about 2 to about 6 hours; essentially, middle notes provide the skeleton of the perfume formulation".

For the purposes of the present invention "base note" fragrances are defined as "fragrances having a low vapor pressure and high retentivity, and when applied to a paper sachet, the scent remains for more than about 6 hours; essentially, base notes provide the characteristic of the perfume formulation.

The terms "top note", "middle note", and "base note" are well recognized by those skilled in the art of fragrance-containing compositions. However, reference to a specific fragrance raw material as a "top note" within the present invention does mean that others skilled in the art of fragrance-containing compositions may not categorize the same ingredient as a "middle note". The same applies to fragrance raw materials referred to as "middle notes" and "base notes".

Typically "fragrance raw materials" comprise inter alia alcohols, ketones, aldehydes, esters, ethers, nitrites, and alkenes such as terpenes. A listing of common "fragrance raw materials" can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) both incorporated herein by reference.

Aldehyde and Ketone Releasing Pro-fragrances

The fragrance delivery systems of the present invention comprise one or more heterocyclic aldehyde-releasing and/or ketone-releasing pro-fragrances, preferably oxazolidines, tertahydro-1,3-oxazines, thiazolidines, or tetrahydro-1,3-thiazines, more preferably oxazolidines, or tertahydro-1,3-oxazines, most preferably oxazolidines.

The pro-fragrances or pro-accords which are suitable for use in the fragrance delivery systems described herein have the formula:

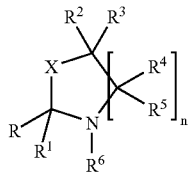

and are capable of releasing an aldehyde fragrance raw material having the formula:

or a ketone fragrance raw material having the formula:

For the purposes of the fragrance delivery systems which comprise one or more heterocyclic pro-fragrances or pro-accords, R units are defined herein as:
a) $C_6$–$C_{22}$, preferably $C_6$–$C_{18}$, more preferably $C_6$–$C_{15}$ substituted or unsubstituted linear alkyl; one or more examples of a fragrance raw material which comprises this unit includes nonanal and decanal;
b) $C_6$–$C_{22}$, preferably $C_6$–$C_{18}$, more preferably $C_6$–$C_{15}$ substituted or unsubstituted branched alkyl; one or more examples of a fragrance raw material which comprises this unit includes 2-methyldecanal;
c) $C_6$–$C_{22}$, preferably $C_6$–$C_{18}$, more preferably $C_6$–$C_{15}$ substituted or unsubstituted linear alkenyl; one or more examples of a fragrance raw material which comprises this unit includes 10-undecenal;
d) $C_6$–$C_{22}$, preferably $C_6$–$C_{18}$, more preferably $C_6$–$C_{15}$ substituted or unsubstituted branched alkenyl; one or more examples of a fragrance raw material which comprises this unit includes citral, melonal, and neral;
e) $C_6$–$C_{22}$, preferably $C_6$–$C_{18}$, more preferably $C_6$–$C_{10}$ substituted or unsubstituted cycloalkyl; one or more examples of a fragrance raw material which comprises this unit includes cyclopentadecanone;
f) $C_6$–$C_{22}$, preferably $C_6$–$C_{15}$, more preferably $C_6$–$C_{15}$ substituted or unsubstituted branched cycloalkyl; one or more examples of a fragrance raw material which comprises this unit includes camphor and muscone;
g) $C_6$–$C_{22}$, preferably $C_6$–$C_{18}$, more preferably $C_6$–$C_{15}$ substituted or unsubstituted cycloalkenyl; one or more examples of a fragrance raw material which comprises this unit includes civetone;
h) $C_6$–$C_{22}$, preferably $C_6$–$C_{18}$, more preferably $C_6$–$C_{15}$ substituted or unsubstituted branched cycloalkenyl; one or more examples of a fragrance raw material which comprises this unit includes α-damascone and β-ionone;
i) $C_6$–$C_{22}$, preferably $C_6$–$C_{18}$, more preferably $C_6$–$C_{10}$ substituted or unsubstituted aryl wherein said aryl unit preferably comprises a phenyl unit; one or more examples of a fragrance raw material which comprises this unit includes benzaldehyde, hydrotropaldehyde and vanillin;
j) $C_6$–$C_{22}$, preferably $C_6$–$C_{15}$, more preferably $C_6$–$C_{15}$ substituted or unsubstituted heterocyclicalkyl;
k) $C_6$–$C_{22}$, preferably $C_6$–$C_{18}$, more preferably $C_6$–$C_{15}$ substituted or unsubstituted heterocyclicalkenyl; one or more examples of a fragrance raw material which comprises this unit includes;
l) and mixtures thereof;

$R^1$ is:
a) hydrogen;
b) $C_1$–$C_{10}$, preferably $C_1$–$C_5$ substituted or unsubstituted linear alkyl;
c) $C_3$–$C_{10}$, preferably $C_3$–$C_5$ substituted or unsubstituted branched alkyl;
d) $C_2$–$C_{10}$, preferably $C_2$–$C_5$ substituted or unsubstituted linear alkenyl;
e) $C_3$–$C_{10}$, preferably $C_4$–$C_{10}$ substituted or unsubstituted branched alkenyl;
f) $C_3$–$C_{15}$, preferably $C_6$–$C_{10}$ substituted or unsubstituted cycloalkyl;
g) $C_4$–$C_{15}$, preferably $C_6$–$C_{10}$ substituted or unsubstituted branched cycloalkyl;
h) $C_4$–$C_{15}$, preferably $C_6$–$C_{10}$ substituted or unsubstituted cycloalkenyl;
i) $C_5$–$C_{15}$, preferably $C_6$–$C_{10}$ substituted or unsubstituted branched cycloalkenyl;
j) $C_6$–$C_{15}$, preferably $C_6$–$C_{10}$ substituted or unsubstituted aryl;
k) $C_6$–$C_{22}$, preferably $C_6$–$C_{10}$ substituted or unsubstituted heterocyclicalkyl;
l) $C_6$–$C_{22}$, preferably $C_6$–$C_{10}$ substituted or unsubstituted heterocyclicalkenyl;

R and $R^1$ can be taken together to form a substituted or unsubstituted ring having in the ring from 3 to 10 carbon atoms; one or more examples of which are substituted cyclopentanone derivatives inter alia hedione and nectaryl; and each $R^2$, $R^3$, $R^6$ and each $R^4$ and $R^5$ pair are independently:
a) $R^1$;
b) hydroxyl;

c) a carbonyl comprising unit having the formula:

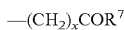

wherein $R^7$ is:
i) —OH, in the case of carboxylic acids;
ii) —$OR^8$, in the case of esters wherein $R^8$ is hydrogen; $C_1$–$C_5$, preferably $C_1$–$C_{10}$, more preferably $C_1$–$C_4$ substituted or unsubstituted linear alkyl; $C_3$–$C_{15}$, preferably $C_3$–$C_{10}$, more preferably $C_3$–$C_4$ substituted or unsubstituted branched alkyl; $C_2$–$C_{22}$, preferably $C_2$–$C_{10}$, more preferably $C_2$–$C_4$ substituted or unsubstituted linear alkenyl; $C_3$–$C_{22}$ substituted or unsubstituted branched alkenyl, or mixtures thereof;
iii) —$N(R^9)_2$ in the case of amides wherein each $R^9$ is independently hydrogen; $C_1$–$C_{15}$, preferably $C_1$–$C_{10}$, more preferably $C_1$–$C_4$ substituted or unsubstituted linear alkyl; $C_3$–$C_{15}$, preferably $C_3$–$C_{10}$, more preferably $C_3$–$C_4$ substituted or unsubstituted branched alkyl; or mixtures thereof;
iv) $C_1$–$C_{22}$, preferably $C_1$–$C_5$ substituted or unsubstituted linear alkyl;
v) $C_1$–$C_{22}$, preferably $C_3$–$C_5$ substituted or unsubstituted branched alkyl;
vi) $C_2$–$C_{22}$, preferably $C_2$–$C_5$ substituted or unsubstituted linear alkenyl;
vii) $C_3$–$C_{22}$, preferably $C_4$–$C_{10}$ substituted or unsubstituted branched alkenyl;
viii) $C_5$–$C_{22}$, preferably $C_6$–$C_{10}$ substituted or unsubstituted cycloalkyl;
ix) $C_6$–$C_{22}$, preferably $C_6$–$C_{10}$ substituted or unsubstituted aryl;
x) $C_6$–$C_{22}$, preferably $C_6$–$C_{10}$ substituted or unsubstituted heterocyclicalkyl;
xi) $C_6$–$C_{22}$, preferably $C_6$–$C_{10}$ substituted or unsubstituted heterocyclicalkenyl;
the index is from 0 to 22;
e) alkyleneoxy units having the formula:

wherein each $R^{10}$, $R^{11}$, and $R^{12}$ is independently;
i) hydrogen;
ii) —OH;
iii) $C_1$–$C_4$ alkyl, preferably methyl;
iv) or mixtures thereof; preferably $R^{10}$, $R^{11}$, and $R^{12}$ are each hydrogen;
$R^{13}$ is:
i) hydrogen;
ii) $C_1$–$C_4$ alkyl, preferably methyl;
iii) or mixtures thereof; preferably $R^{13}$ is methyl or hydrogen, more preferably hydrogen;
$R^{14}$ is:
i) hydrogen;
ii) $C_1$–$C_4$ alkyl, preferably methyl;
iii) or mixtures thereof; preferred $R^{14}$ is hydrogen;
$R^{10}$ and $R^{11}$ can be taken together to form a $C_3$–$C_6$ spiroannulated ring, carbonyl unit, or mixtures thereof; y has the value from 0 to 10, z has the value from 1 to 50;
f) any two $R^2$, $R^3$, $R^4$, $R^5$, or $R^6$ units can be taken together, and where feasible, combined to form:
i) a carbonyl moiety;
ii) a $C_3$–$C_6$ spiroannulated ring;
iii) a heterocyclic aromatic ring comprising from 5 to 7 atoms;
iv) a non-heterocyclic aromatic ring comprising from 5 to 7 atoms;
v) a heterocyclic ring comprising from 5 to 7 atoms;
vi) a non-heterocyclic ring comprising from 5 to 7 atoms;
vii) or mixtures thereof;
g) and mixtures thereof;
the index n is an integer from 1 to 3, preferably 1 or 2, more preferably 1.

For the purposes of the present invention, the term "substituted" is defined herein as "compatible moieties which replace a hydrogen atom". For the purposes of the present invention, hydrogens which are substitutable are labeled as R' units in the following examples. Non-limiting examples of substituents which can replace hydrogen atoms are $C_1$–$C_{22}$ linear or branched hydrocarbyl units inter alia alkyl, alkenyl; hydroxy, nitrilo, nitro, carboxyl (—CHO; —$CO_2H$; —$CO_2R''$; —$CONH_2$; —CONHR''; —$CONR''_2$; wherein R'' is $C_1$–$C_{12}$ linear or branched alkyl), amino, $C_1$–$C_{12}$ mono- and dialkylamino, and mixtures thereof. However, the formulator may wish to include other substituents not specifically mentioned herein. Not each hydrogen of a substituted unit, i.e., substituted linear alkyl, must be substituted; only one hydrogen must be substituted by another moiety for a unit to be "substituted" for the purposes of the present invention.

However, more than one definition may apply to a unit which is suitable for use in the pro-fragrances of the present invention. For example, as defined herein above, R may be a $C_6$–$C_{22}$ substituted or unsubstituted, linear or branched alkyl moiety. The unit 3-propylheptyl, which comprises 10 carbon atoms may be considered a $C_{10}$ branched alkyl unit or a $C_7$ linear alkyl unit having a hydrogen atom substituted by a $C_3$ alkyl unit. Either definition applies equally well for the purposes of the present invention.

The present invention further relates to heterocyclic pro-fragrances, preferably oxazolidines and tetrahydro-1,3-oxazines, having the formula:

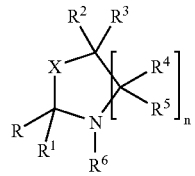

wherein said pro-fragrance or pro-accord releases an aldehyde or a ketone fragrance raw material, wherein X is oxygen or sulfur; R is:
a) $C_6$–$C_{22}$ substituted or unsubstituted linear alkyl;
b) $C_6$–$C_{22}$ substituted or unsubstituted branched alkyl;
c) $C_6$–$C_{22}$ substituted or unsubstituted linear alkenyl;
d) $C_6$–$C_{22}$ substituted or unsubstituted branched alkenyl;
e) $C_6$–$C_{22}$ substituted or unsubstituted cycloalkyl;
f) $C_6$–$C_{22}$ substituted or unsubstituted branched cycloalkyl;
g) $C_6$–$C_{22}$ substituted or unsubstituted cycloalkenyl;
h) $C_6$–$C_{22}$ substituted or unsubstituted branched cycloalkenyl;
i) $C_6$–$C_{22}$ substituted or unsubstituted aryl;
j) $C_6$–$C_{22}$ substituted or unsubstituted heterocyclicalkyl;
k) $C_6$–$C_{22}$ substituted or unsubstituted heterocyclicalkenyl;
l) and mixtures thereof;
$R^1$ is:
a) hydrogen;
b) $C_1$–$C_{10}$ substituted or unsubstituted linear alkyl;

c) $C_3$–$C_{10}$ substituted or unsubstituted branched alkyl;
d) $C_2$–$C_{10}$ substituted or unsubstituted linear alkenyl;
e) $C_3$–$C_{10}$ substituted or unsubstituted branched alkenyl;
f) $C_4$–$C_{15}$ substituted or unsubstituted cycloalkyl;
g) $C_4$–$C_{15}$ substituted or unsubstituted branched cycloalkyl;
h) $C_5$–$C_{15}$ substituted or unsubstituted cycloalkenyl;
i) $C_5$–$C_{15}$ substituted or unsubstituted branched cycloalkenyl;
j) $C_6$–$C_{15}$ substituted or unsubstituted aryl;
k) $C_6$–$C_{22}$ substituted or unsubstituted heterocyclicalkyl;
l) $C_6$–$C_{22}$ substituted or unsubstituted heterocyclicalkenyl;
m) and mixtures thereof;
R and $R^1$ can be taken together to form a substituted or unsubstituted ring having in the ring from 3 to 10 carbon atoms;
each $R^2$, $R^3$, and each $R^4$ and $R^5$ pair are independently:
a) $R^1$;
b) hydroxyl;
c) a carbonyl comprising unit having the formula:

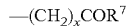

wherein $R^7$ is:
i) —OH;
ii) —$OR^8$ wherein $R^8$ is hydrogen, $C_1$–$C_{15}$ substituted or unsubstituted linear alkyl, $C_1$–$C_{15}$ substituted or unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen;
iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
iv) $C_1$–$C_{22}$ substituted or unsubstituted linear alkyl;
v) $C_1$–$C_{22}$ substituted or unsubstituted branched alkyl;
vi) $C_2$–$C_{22}$ substituted or unsubstituted linear alkenyl;
vii) $C_3$–$C_{22}$ substituted or unsubstituted branched alkenyl;
viii) $C_5$–$C_{22}$ substituted or unsubstituted cycloalkyl;
ix) $C_6$–$C_{22}$ substituted or unsubstituted aryl;
x) $C_6$–$C_{22}$ substituted or unsubstituted heterocyclicalkyl;
xi) $C_6$–$C_{22}$ substituted or unsubstituted heterocyclicalkenyl;
the index x is from 0 to 22;
d) alkyleneoxy units having the formula:

wherein each $R^{10}$, $R^{11}$, and $R^{12}$ is independently;
i) hydrogen;
ii) —OH;
iii) $C_1$–$C_4$ alkyl;
iv) or mixtures thereof;
$R^{13}$ is:
i) hydrogen;
ii) $C_1$–$C_4$ alkyl;
iii) or mixtures thereof;
$R^{14}$ is:
i) hydrogen;
ii) $C_1$–$C_4$ alkyl;
iii) or mixtures thereof;
$R^{10}$ and $R^{11}$ can be taken together to form a $C_3$–$C_6$ spiroannulated ring, carbonyl unit, or mixtures thereof; y has the value from 0 to 10, z has the value from 1 to 50;
e) and mixtures thereof;

$R^6$ is:
a) $C_1$–$C_{10}$ substituted linear alkyl;
b) $C_3$–$C_{10}$ substituted branched alkyl;
c) $C_2$–$C_{10}$ substituted or unsubstituted linear alkenyl;
d) $C_3$–$C_{10}$ substituted or unsubstituted branched alkenyl;
e) $C_3$–$C_{15}$ substituted cycloalkyl;
f) $C_4$–$C_{15}$ substituted or unsubstituted branched cycloalkyl;
g) $C_4$–$C_{15}$ substituted or unsubstituted cycloalkenyl;
h) $C_5$–$C_{15}$ substituted or unsubstituted branched cycloalkenyl;
i) $C_6$–$C_{15}$ substituted aryl;
j) $C_6$–$C_{22}$ substituted or unsubstituted heterocyclicalkyl;
k) $C_6$–$C_{22}$ substituted or unsubstituted heterocyclicalkenyl;
l) a carbonyl comprising unit having the formula:

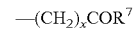

wherein $R^7$ is:
i) —OH;
ii) —$OR^8$ wherein $R^8$ is hydrogen, $C_1$–$C_{15}$ substituted linear alkyl, $C_{11}$–$C_{15}$ unsubstituted linear alkyl, $C_1$–$C_{15}$ substituted branched alkyl, $C_{11}$–$C_{15}$ unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen or thioalkyl;
iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
iv) $C_1$–$C_{22}$ substituted or unsubstituted linear alkyl;
v) $C_1$–$C_{22}$ substituted or unsubstituted branched alkyl;
vi) $C_2$–$C_{22}$ substituted or unsubstituted linear alkenyl;
vii) $C_3$–$C_{22}$ substituted or unsubstituted branched alkenyl;
viii) $C_5$–$C_{22}$ substituted or unsubstituted cycloalkyl;
ix) $C_6$–$C_{22}$ substituted or unsubstituted aryl;
x) $C_6$–$C_{22}$ substituted or unsubstituted heterocyclicalkyl;
xi) $C_6$–$C_{22}$ substituted or unsubstituted heterocyclicalkenyl;
the index x is from 0 to 22;
m) alkyleneoxy units having the formula:

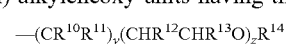

wherein each $R^{10}$, $R^{11}$, and $R^{12}$ is independently;
i) hydrogen;
ii) —OH;
iii) $C_1$–$C_4$ alkyl;
iv) or mixtures thereof;
$R^{13}$ is:
i) hydrogen;
ii) $C_1$–$C_4$ alkyl;
iii) or mixtures thereof;
$R^{14}$ is:
i) hydrogen;
ii) $C_1$–$C_4$ alkyl;
iii) or mixtures thereof;
$R^{10}$ and $R^{11}$ can be taken together to form a $C_3$–$C_6$ spiroannulated ring, carbonyl unit, or mixtures thereof; y has the value from 0 to 10, z has the value from 1 to 50;
n) and mixtures thereof;
any two $R^2$, $R^3$, $R^4$, $R^5$, or $R^6$ units can be taken together to form:
i) a carbonyl moiety;
ii) a $C_3$–$C_6$ spiroannulated ring;

iii) a heterocyclic aromatic ring comprising from 5 to 7 atoms;

iv) a non-heterocyclic aromatic ring comprising from 5 to 7 atoms;

v) a heterocyclic ring comprising from 5 to 7 atoms;

vi) a non-heterocyclic ring comprising from 5 to 7 atoms;

vii) or mixtures thereof; and the index n is an integer from 1 to 3.

The pro-fragrance compounds of the present invention do not comprise a halogen nor does the $R^6$ unit comprise a thioalkyl moiety.

A non-limiting example of an aldehyde-releasing pro-fragrance suitable for use in the fragrance delivery systems according to the present invention is 1,3-oxazine having the formula:

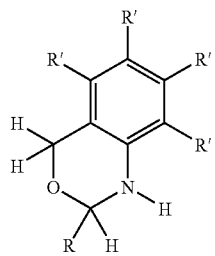

wherein $R^1$, $R^2$, $R^3$ and $R^6$ are each hydrogen; n is equal to 2, therefore the pro-fragrance comprises two sets of $R^4$ and $R^5$ units, and wherein further the first pair of $R^4$ and $R^5$ units are taken together with the second pair of $R^4$ and $R^5$ units to form a fused aromatic ring having 6 carbon atoms. R' indicates substitutable hydrogens.

A further non-limiting example of an aldehyde-releasing pro-fragrance fragrance suitable for use in the fragrance delivery systems according to the present invention is the oxazolidine having the formula:

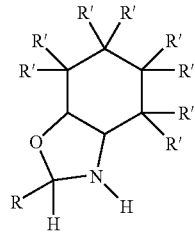

wherein $R^1$ and $R^6$ are each hydrogen; n is equal to 1, $R^3$ and $R^5$ are each hydrogen, and the $R^2$ unit is taken together with the $R^4$ unit to form a substituted cycloalkyl ring having 6 carbon atoms, wherein further R' indicates substitutable hydrogens.

A non-limiting example of a ketone-releasing pro-fragrance fragrance suitable for use in the fragrance delivery systems according to the present invention is the fused ring compound having the formula:

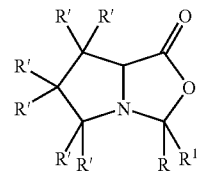

wherein n is equal to 1, $R^4$ is equal to hydrogen, $R^2$ and $R^3$ are taken together to form a carbonyl unit, and the $R^5$ unit is taken together with the $R^6$ unit to form a substituted cycloalkyl ring having 5 atoms, wherein further R' indicates substitutable hydrogens.

An example of a prefered heterocyclic pro-fragrance according to the present invention is 2-(2,4-dimethylcyclo-hex-3-enyl)-5-carboxymethyl-N-isopropyl-1,3-oxazolidine having the formula:

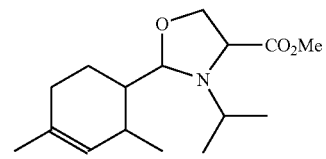

which is obtained from the reaction of N-isopropyl serine methyl ester and triplal.

One class of preferred pro-fragrances of the present invention are the tertiary α-carbon 1,3-oxazolindines having the formula:

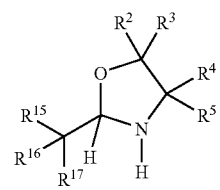

wherein $R^2$, $R^3$, $R^4$, and $R^5$ is the same as defined herein above, $R^{15}$, $R^{16}$, and $R^{17}$ are each independently:

a) $C_1$–$C_{22}$ substituted or unsubstituted linear alkyl, preferably methyl or ethyl, more preferably methyl;

b) $C_3$–$C_{22}$ substituted or unsubstituted branched alkyl;

c) $C_2$–$C_{22}$ substituted or unsubstituted linear alkenyl;

d) $C_3$–$C_{22}$ substituted or unsubstituted branched alkenyl;

e) $C_3$–$C_{22}$ substituted or unsubstituted cycloalkyl;

f) $C_4$–$C_{22}$ substituted or unsubstituted branched cycloalkyl;

g) $C_4$–$C_{22}$ substituted or unsubstituted cycloalkenyl;

h) $C_4$–$C_{22}$ substituted or unsubstituted branched cycloalkenyl;

i) $C_6$–$C_{22}$ substituted or unsubstituted aryl;

j) $C_6$–$C_{22}$ substituted or unsubstituted heterocyclicalkyl;

k) $C_6$–$C_{22}$ substituted or unsubstituted heterocyclicalkenyl;

l) any two $R^{15}$, $R^{16}$, and $R^{17}$ units can be taken together to form a substituted or unsubstituted ring having from 3–10 carbon atoms;

m) and mixtures thereof;

Preferably one $R^{15}$, $R^{16}$, or $R^{17}$ unit, more preferably two $R^{15}$, $R^{16}$, or $R^{17}$ unit is methyl.

A non-limiting example of an α-carbon tertiary 1,3-oxazolidine pro-fragrance has the formula:

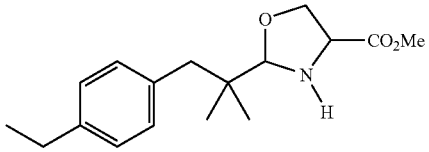

wherein said pro-fragrance is formed from serine methyl ester and florhydral.

Non-limiting examples of aldehydes which can be suitably released by the pro-fragrances of the present invention include phenylacetaldehyde, p-methyl phenylacetaldehyde, p-isopropyl phenylacetaldehyde, methylnonyl acetaldehyde, phenylpropanal, 3-(4-t-butylphenyl)-2-methyl propanal (Lilial), 3-(4-t-butylphenyl)-propanal (Bourgeonal), 3-(4-methoxyphenyl)-2-methylpropanal (Canthoxal), 3-(4-isopropylphenyl)-2-methylpropanal (Cymal), 3-(3,4-methylenedioxyphenyl)-2-methylpropanal (Helional), 3-(4-ethylpheny)-2,2-dimethylpropanal (Floralozone), phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (Melonal), 2,4-heptadienal, octanal, 2-octenal, 3,7-dimethyloctanal, 3,7-dimethyl-2,6-octadien-1-al, 3,7-dimethyl-1,6-octadien-3-al, 3,7-dimethyl-6-octenal (citronellal), 3,7-dimethyl-7-hydroxyoctan-1-al (hydroxy citronellal), nonanal, 6-nonenal, 2,4-nonadienal, 2,6-nonadienal, decanal, 2-methyl decanal, 4-decenal, 9-decenal, 2,4-decadienal, undecanal, 2-methyldecanal, 2-methylundecanal, 2,6,10-trimethyl-9-undecenal (Adoxal), undec-10-enyl aldehyde, undec-8-enanal, dodecanal, tridecanal, tetradecanal, anisaldehyde, bourgenonal, cinnamic aldehyde, α-amylcinnam-aldehyde, α-hexyl cinnamaldehyde, methoxy-cinnamaldehyde, isocyclocitral, citronellyl oxyacet-aldehyde, cortexaldehyde, cumminic aldehyde, cyclamen aldehyde, florhydral, heliotropin, hydrotropic aldehyde, vanillin, ethyl vanillin, benzaldehyde, p-methyl benzaldehyde, 3,4-dimethoxybenzaldehyde, 3- and 4-(4-hydroxy-4-methyl-pentyl)-3-cyclohexene-1-carboxaldehyde (Lyral), 2,4-dimethyl-3-cyclohexene-1-carboxaldehyde (Triplal), 1-methyl-3-(4-methylpentyl)-3-cyclohexencarboxaldehyde (Vernaldehyde), p-methylphenoxyacetaldehyde (Xi aldehyde), and mixtures thereof.

Non-limiting examples of ketones which can be suitably released by the pro-fragrances of the present invention include α-damascone, β-damascone, δ-damascone, β-damascenone, muscone, 6,7-dihydro-1,1,2,3,3-pentamethyl-4(5H)-indanone (cashmeran), cis-jasmone, dihydrojasmone, α-ionone, β-ionone, dihydro-β-ionone, γ-methyl ionone, α-iso-methyl ionone, 4-(3,4-methylenedioxyphenyl)butan-2-one, 4-(4-hydroxyphenyl)butan-2-one, methyl β-naphthyl ketone, methyl cedryl ketone, 6-acetyl-1,1,2,4,4,7-hexamethyltetralin (tonalid), l-carvone, 5-cyclohexadecen-1-one, acetophenone, decatone, 2-[2-(4-methyl-3-cyclohexenyl-1-yl)propyl]cyclopentan-2-one, 2-sec-butylcyclohexanone, β-dihydro ionone, allyl ionone, α-irone, α-cetone, α-irisone, acetanisole, geranyl acetate, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, ethyl amyl ketone, ethyl pentyl ketone, menthone, methyl-7,3-dihydro-2H-1,5-benzodioxepine-3-one, fenchone, and mixtures thereof.

Fragrance Delivery System

The present invention further relates to fragrance delivery systems which are suitable for use in delivering an enhanced duration aesthetic benefit. The fragrance delivery systems are suitable for use and are compatible with any composition which may require a fragrance inter alia fine fragrances, perfumes, personal care products, deodorants, shampoos, laundry detergents, malodor masking agents.

In general, the compositions of the present invention, other than fine fragrances or perfumes which are described herein below, comprise from about 0.01%, preferably from about 0.05%, more preferably from about 0.1%, most preferably from about 0.5% to about 10%, preferably to about 7%, more preferably to about 5%, most preferably to about 3% by weight, of a fragrance delivery system comprising:

A) from about 1%, preferably from about 10%, more preferably from about 25% to about 100%, preferably to about 90%, more preferably to about 75%, most preferably to about 50% by weight, of a pro-fragrance component comprising:
  i) at least 1% by weight (10 ppb of the composition which employs the fragrance delivery system), of an aldehyde or ketone releasing pro-fragrance component according to the present invention as described herein;
  ii) optionally at least 1% by weight (10 ppb of the composition which employs the fragrance delivery system), of one or more pro-accords formed from at least one fragrance raw material, wherein said pro-accord is selected from the group consisting of acetals, ketals, orthoesters, orthocarbonates, and mixtures thereof, each pro-accord releasing upon hydrolysis said fragrance raw material from which it is formed, said fragrance raw materials selected from the group consisting of primary, secondary, and tertiary alcohols, aldehydes, ketones, esters, carbonates, and mixtures thereof, provided each pro-accord:
    a) is formed from at least one fragrance raw material having a molecular weight greater than or equal to about 100 g/mol;
    b) has a fragrance release half-life of greater than or equal to about 0.1 hours at pH 5.3 and less than or equal to about 12 hours at pH 2.5 when measured in $NaH_2PO_4$ buffer;
  iii) the balance carriers, stabilizers, and other adjunct ingredients; and
B) optionally from about 1%, preferably from about 25% to about 99%, preferably to about 90%, more preferably to about 75%, most preferably to about 50% by weight, a fragrance raw material component comprising:
  i) optionally at least 1% by weight, of a mixture of one or more base note fragrances;
  ii) optionally at least 1% by weight, of a mixture of one or more top or middle note fragrances;
  ii) optionally the balance carriers, fixatives, and other adjunct ingredients.

However, some compositions according to the present invention are fine fragrances or perfumes. These embodiments typically comprise only fragrance raw materials, pro-fragrances, pro-accords, carriers, and stabilizers. The fine fragrance and perfume compositions which utilize the cyclic pro-fragrances of the present invention comprise:

a) at least 0.01%, preferably from about 0.1%, more preferably from about 5%, most preferably from about 20% to about 100%, preferably to about 75%, more preferably to 50% by weight, of an aldehyde or ketone releasing pro-fragrance component according to the present invention;

b) optionally from about 1%, preferably from about 25% to about 99.99%, preferably to about 99.9%, more preferably to about 95%, most preferably to about 50% by weight, of one or more pro-accords which comprise n fragrance raw materials but which release n+1 fragrance raw materials, preferably orthoesters, orthocarbonates, β-ketoesters, and mixtures thereof;

c) optionally from about 1%, preferably from about 25% to about 99.99%, preferably to about 99.9%, more preferably to about 95%, most preferably to about 50% by weight, of one or more pro-fragrances selected from the group consisting of acetals, ketals, orthoesters, orthocarbonate, ortholactones, β-ketoesters, and mixtures thereof;

d) optionally from about 1%, preferably from about 25% to about 99.99%, preferably to about 99.9%, more preferably to about 95%, most preferably to about 50% by weight, of one or more fragrance raw materials, preferably one or more fragrance raw materials which are released by a pro-fragrance or pro-accord which comprises the fragrance delivery system; and e) optionally one or more carriers, fixatives, stabilizers, or adjunct ingredients.

When present, the carriers, fixatives, or stabilizers will comprise the balance of the compositions. Typical carriers are methanol, ethanol (preferred), iso-propanol, polyethylene glycol, as well as water in some instances, especially as a vehicle to deliver materials which provide reserve alkalinity to the fragrance delivery system. Fixatives serve to lower the volatility of certain top and middle notes in order to extend their contact time on skin. Adjunct ingredients include perfume raw material components which are essential oils and are therefore not a single chemical entity. In addition, the adjunct ingredients may be mixtures of materials which serve a purpose in addition to providing a pleasurable odor (i.e., an astringent in a personal hygiene article).

For the purposes of the fragrance delivery systems of the present invention, a "pro-accord which comprises n fragrance raw materials but which releases n+1 fragrance raw materials" is defined as "a compound which is prepared from one or more fragrance raw materials, said fragrance raw material being chemically transformed into a "releasable form" such that when said releasable form breaks down, the original fragrance raw material is released as well as at least one other fragrance raw material which was not a starting material used in forming the releasable form". The term "releasable form" is defined herein as a "pro-fragrance or pro-accord compound, which ever form is applicable". Non-limiting examples of "releasable forms" or pro-accords which satisfy the n+1 requirement are as follows.

The pro-accord tris(9-decenyl) orthoformate is prepared by treating 9-decenol (i.e., Rosalva), which is a fragrance raw material as defined herein, with a suitable amount of triethyl orthoformate, not a fragrance raw material as defined herein, in the presence of an acid catalyst optionally in the presence of a solvent. Tris(9-decenyl) when exposed to suitable conditions (e.g., exposure to the acid mantle of human skin) breaks down to release a mixture of 9-decenol and 9-decenyl formate, both of which are fragrance raw materials. Therefore, one fragrance raw material is used to prepare a releasable form (pro-accord) of two fragrance raw materials.

The pro-accord 3,7-dimethyl-1,6-octadien-3-yl 3-(β-naphthyl)-3-oxo-propionate, which is a β-ketoester pro-accord, is prepared by treating 3,7-dimethyl-1,6-octadien-3-ol (linalool), which is a fragrance raw material according to the present invention, with diketene under suitable conditions to form intermediate 3,7-dimethyl-1,6-octadien-3-yl 3-oxo-butyrate, which is subsequently treated with 2-naphthoyl chloride to yield the pro-accord. 3,7-Dimethyl-1,6-octadien-3-yl 3-(β-naphthyl)-3-oxo-propionate when exposed to suitable conditions (e.g., exposure to nascent moisture) breaks down to release a mixture of linalool and methyl β-naphthyl ketone, both of which are fragrance raw materials as defined herein.

As described herein above, an optional component of the fragrance delivery systems of the present invention are pro-fragrances or pro-accords which are not heterocyclic aldehyde and/or ketone releasing pro-fragrances. The optional pro-accords or pro-fragrances are equally functional in either personal care compositions inter alia lotions, creams, deodorants or personal fragrance compositions inter alia fine fragrances, perfumes.

Preferred optional pro-accords and/or pro-fragrances include, but are not limited to, orthoesters, orthocarbonates, acetals, ketals, ortholactones, and β-ketoesters.

Non-limiting examples of optional orthoesters which are suitable for use in the fragrance delivery systems of the present invention include tris-geranyl orthoformate, tris(cis-3-hexen-1-yl) orthoformate, tris(phenylethyl) orthoformate, bis(citronellyl) ethyl orthoacetate, tris(citronellyl) orthoformate, tris(cis-6-nonenyl) orthoformate, tris(phenoxyethyl) orthoformate, tris(geranyl, neryl) orthoformate (70:30 geranyl:neryl), tris(9-decenyl) orthoformate, tris(3-methyl-5-phenylpentanyl) orthoformate, tris(6-methylheptan-2-yl) orthoformate, tris([4-(2,2,6-trimethyl-2-cyclohexen-1-yl)-3-buten-2-yl] orthoformate, tris[3-methyl-5-(2,2,3-trimethyl-3-cyclopenten-1-yl)4-penten-2-yl] orthoformate, trismenthyl orthoformate, tris(4-isopropylcyclohexylethyl-2-yl) orthoformate, tris-(6,8-dimethylnonan-2-yl) orthoformate, tris-phenylethyl orthoacetate, tris(cis-3-hexen-1-yl) orthoacetate, tris(cis-6-nonenyl) orthoacetate, tris-citronellyl orthoacetate, bis(geranyl) benzyl orthoacetate, tris(geranyl) orthoacetate, tris(4-isopropylcyclohexylmethyl) orthoacetate, tris(benzyl) orthoacetate, tris(2,6-dimethyl-5-heptenyl) orthoacetate, bis(cis-3-hexen-1-yl) amyl orthoacetate, and neryl citronellyl ethyl orthobutyrate.

Non-limiting examples of optional orthocarbonates which are suitable for use in the fragrance delivery systems of the present invention include bis(ethyl) bis(geranyl) orthocarbonate, bis(ethyl) bis(phenylethyl) orthocarbonate, bis (ethyl) bis(cis-3-hexenyl) orthocarbonate, bis(ethyl) bis(citronellyl) orthocarbonate, bis(ethyl) bis(linalyl) orthocarbonate, bis(ethyl) bis(menthyl) orthocarbonate, bis (dodecyl) bis(geranyl) orthocarbonate, and bis(dodecyl) bis (phenylethyl) orthocarbonate.

Non-limiting examples of optional acetals which are suitable for use in the fragrance delivery systems of the present invention include bis(cis-3-hexenyl) vanillin, bis (geranyl) cinnamaldehyde acetal, bis(2-phenylethyl) anisaldehyde acetal, bis (citronellyl) cyclamen aldehyde acetal, and bis(citronellyl) citral acetal.

Non-limiting examples of optional ketals which are suitable for use in the fragrance delivery systems of the present invention include bis(linalyl) β-ionone ketal, bis(dihydromyrcenyl) α-damascone ketal, bis(linalyl) 6,7-dihydro- 1,1,2,3,3-pentamethyl-4(5H)-indanone ketal, bis(dihydromyrcenyl) β-ionone ketal, and bis(citronellyl) cis-jasmone ketal.

Non-limiting examples of optional β-ketoesters which are suitable for use in the fragrance delivery systems of the present invention include 2,6-dimethyl-7-octen-2-yl 3-(4-methoxyphenyl)-3-oxo-propionate, 3,7-dimethyl-1,6-octadien-3-yl 3-(α-naphthyl)-3-oxo-propionate, 2,6-dimethyl-7-octen-2-yl 3-(4-methoxyphenyl)-3-oxo-propionate, cis 3-hexen-1-yl 3-(β-naphthyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, and 3,7-dimethyl-2,6-octadienyl 3-heptyl-3-oxo-propionate.

Fragrance Release Half-life

One aspect of the present invention which is a key element in providing the formulator with a method for determining the manner in which a pro-fragrance according to the present invention releases its fragrance raw material, is the measurement of the pro-fragrance "Fragrance Release Half-Life, (FRHL). The pro-fragrances useful in the personal care compositions of the present invention generally have a delayed release of final fragrance raw material in order to achieve the increased fragrance longevity benefits described herein. However, the pro-fragrances generally also deliver the fragrance raw materials during a time period useful to the formulator, for example, within a time period desirable to the consumer.

For the purposes of the present invention the pro-accords generally have a FRHL of less than or equal to 12 hours when measured in $NaH_2PO_4$ buffer at pH 2.5 and greater than or equal to 0.1 hour when measured in $NaH_2PO_4$ buffer at pH 5.3. The "Fragrance Release Half-life" is defined herein as follows.

Pro-fragrances deliver their corresponding mixture of fragrance raw materials or fragrance accords according to the equation:

Pro-Fragrance→Fragrance Raw Material wherein the fragrance raw material which is released may be released as a single component or a multiple fragrance raw material accord.

The rate at which the fragrance is released is defined by the formula:

Rate=k[Pro-fragrance]

and can be further expressed by the formula:

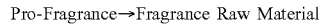

wherein k is the release rate constant and [Pro-fragrance] is the concentration of pro-fragrance. For the purposes of the present invention the "Fragrance Release Half-life", $t_{1/2}$, is related to the release rate constant by the formula:

$$t_{1/2} = \frac{0.693}{k}$$

and this relationship is used for the purposes of the present invention to determine the "FRHL.

Due to the hydrophobic nature of some pro-accords, it is necessary to conduct the determination of $t_{1/2}$ and k in a mixture of 90/10 dioxane/phosphate buffered water. The phosphate buffered water is prepared by admixing 3.95 mL of 85% phosphoric acid ($H_3PO_4$) and 24 g of sodium dihydrogen phosphate ($NaH_2PO_4$) with one liter of water. The pH of this solution is approximately 2.5. Next 10 mL of the phosphate buffer is admixed with 90 mL of dioxane and the pro-fragrance to be analyzed is added. The hydrolysis kinetics are then monitored by conventional HPLC at 30° C.

In some instances, it is desirable to formulate a fragrance delivery system having one or more pro-fragrances which deliver a rapid release of fragrance raw material in addition to the delayed onset of a fragrance. In such cases the hydrolysis rate, and therefore the determination of $t_{1/2}$ must be measured in a buffer system which can accommodate this more rapid hydrolysis rate.

The pro-fragrances of the present invention are stable under pH conditions encountered in the formulation and storage of fine perfume, personal care and personal hygiene articles which have a pH of from about 7.1 to 11.5, and during solution-use of such products. Due to their high molecular weight and hydrophobicity, these pro-fragrances and/or pro-accords remain deposited upon skin even when exposed to water (i.e. when formulated into a sun screen). Because the pro-fragrances are subject to hydrolysis when the pH is reduced, they hydrolyze to release their component fragrance compounds when applied to skin or are exposed even to reduced pH such as present in air and humidity. The reduction in pH should be at least 0.1, preferably at least about 0.5 units. Preferably the pH is reduced by at least 0.5 units to a pH of 7.5 or less, more preferably 6.9 or less. Preferably, the solution in which the pro-accord is applied is alkaline.

Odor Value

The pro-fragrances of the present invention typically have an Odor Value greater than or equal to about 1, preferably greater than or equal to about 5, more preferably greater than or equal to about 10. The term "Odor Value" is defined by the following formula:

$$OV = \frac{[\text{Concentration of } FRM]}{ODT}$$

wherein OV is the odor value of the fragrance raw material released upon the skin by the pro-accord. The odor value is the concentration of the fragrance raw material, FRM, on the skin surface divided by the Odor Detection Threshold, ODT. The term "level of noticeability" is often applied to and/or substituted for the term "odor value".

Odor Detection Threshold

For the purposes of the present invention the term "odor detection threshold" is defined as the level at which a fragrance raw material is perceptible to the average human. The odor detection threshold (ODT) of the compositions of the present invention are preferably measured by carefully controlled gas chromatograph (GC) conditions as described hereinbelow. The preferred fragrance raw materials of the present invention have an ODT of at least about 100 part per billion (ppb), more preferably 10 ppb, most preferably 1 ppb. Fragrance raw materials having an ODT greater than 10 parts per million (ppm) are typically avoided unless useful as an adjunct ingredient, for example, as an adjunct alcohol when adjusting the fragrance release half-life of an orthoester.

Determination of Odor Detection Thresholds is as follows. A gas chromatograph is characterized to determine the exact volume of material injected by a syringe, the precise split ratio, and the hydrocarbon response using a hydrocarbon standard of known concentration and chain-length distribution. The air flow rate in accurately measured and, assuming the duration of a human inhalation to last 0.02 minutes, the sampled volume is calculated. Since the precise concentration at the detector at any point in time is known, the mass per volume inhaled is known and hence the concentration of material. To determine whether a material has a threshold below 10 ppb, solutions are delivered to the sniff port at the back-calculated concentration. A panelist sniffs the GC effluent and identifies the retention time when odor is notice. The average over all panelists determines the threshold of noticeability or ODT. The necessary amount of analyte is injected onto the column to achieve a 10 ppb concentration at the detector. Typical gas chromatograph parameters for determining odor detection thresholds are listed below.

GC: 5890 Series II with FID detector 7673 Autosampler
Column: J&W Scientific DB-1, length 30 m, i.d. 0.25 mm, film thickness 1 μm.
Split Injection: 17/1 split ratio
Autosampler: 1.13 μl/injection
Column flow: 1.10 mL/min
Airflow: 345 mL/min
Inlet temperature: 245° C.
Detector temperature: 285° C.
Temperature Information:
  Initial temperature: 50° C.
  Rate: 5° C./min
  Final temperature: 280° C.
  Final time: 6 min
Leading assumptions: 0.02 minutes per sniff and that GC air adds to sample dilution.

Skin Performance Index

Although a pro-fragrance or pro-accord may comprise a fragrance release half-life which ensures delivery of a fragrance raw material during a period of time useful to the formulator, unless the fragrance raw materials which comprise said fragrance delivery system have ODT values large enough to be perceived by the user, the formulator will be compelled to use an inordinate amount of material to achieve a suitable fragrance level.

The pro-fragrances of the present invention have a Skin Performance Index (SPI) greater than or equal to 0.1, preferably greater than or equal to 0.5. The Skin Performance Index is defined by the following:

$$SPI = \frac{[Odor\ Value]^*}{t_{1/2}}$$

wherein the term [Odor Value]* is the estimated concentration of the fragrance raw material in the headspace above a solution of the fragrance raw material as measured in a 1% solution of ethanol, and $t_{1/2}$ is the fragrance release half-life measured at pH 5.3 in the above described buffer. For the purposes of the present invention, the $t_{1/2}$ of the SPI is measured at 5.3 and the value of the fragrance release half-life is preferably from 0.1 hours to 60 hours.

The [Odor Value]* is an estimation of the vapor pressure of the fragrance raw material using empirically determined KOVATS indices. "The Vapor Pressures of Pure Substances", T. Boublik et al., Elseiver, N.Y. (1973) incorporated herein by reference, describes an index line for normal alkanes wherein $C_{10}$ is equal to 30,000 ppb, $C_{12}$ is equal to 3,000 ppb, $C_{14}$ is equal to 300 ppb, $C_{16}$ is equal to 30 ppb, etc. Using these values as reference standards, the KOVATS index of a fragrance raw material is obtained from gas chromatographic analysis of the FRM and the experimental index is then used to determine the relative vapor pressure and hence the head space concentration of the fragrance raw material.

"New Method for Estimating Vapor Pressure by the Use of Gas Chromatography" J. Chromatography A, 79 p 123–129, (1996) and "Simple and Versatile Injection System for Capillary Gas Chromatographic Columns: Performance Evaluation of a System Including Mass Spectrometric and Light Pipe Fourier-Transform Infrared Detection", J. Chromatography A, 713, p 201–215, (1996) included herein by reference, further describe methods and techniques suitable for use in determining the vapor pressure and head space concentration of FRM's as they relate to the term [Odor Value]* of the present invention.

Using the criteria set forth in the present invention inter alia fragrance release half-life, odor value, odor detection threshold, skin performance index, the formulator is able to fashion an aldehyde or ketone releasing cyclic pro-fragrance. By manipulation of the $R^2$, $R^3$, $R^4$, $R^5$ and $R^6$ units of the cyclic pro-fragrances of the present invention, the release rate of either an aldehyde or ketone fragrance raw material can be adjusted. Several different pro-fragrances which release the same fragrance raw material, but at differing rates or levels, can be admixed to further prolong or extend the period of fragrance raw material delivery.

The present invention also relates to a method for preparing a fragrance delivery system or a pro-fragrance component of a fragrance delivery system. In general, the process of the present invention comprises the steps of:

a) admixing one or more precursors of the formula:

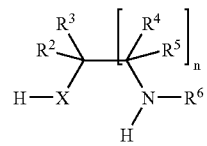

wherein X is oxygen or sulfur; each $R^2$, $R^3$, $R^6$ and each $R^4$ and $R^5$ pair are independently:
a) hydrogen;
b) $C_1$–$C_{10}$ substituted or unsubstituted linear alkyl;
C) $C_3$–$C_{10}$ substituted or unsubstituted branched alkyl;
d) $C_2$–$C_{10}$ substituted or unsubstituted linear alkenyl;
e) $C_3$–$C_{10}$ substituted or unsubstituted branched alkenyl;
f) $C_3$–$C_{15}$ substituted or unsubstituted cycloalkyl;
g) $C_4$–$C_{15}$ substituted or unsubstituted branched cycloalkyl;
h) $C_4$–$C_{15}$ substituted or unsubstituted cycloalkenyl;

i) $C_5$–$C_{15}$ substituted or unsubstituted branched cycloalkenyl;
j) $C_6$–$C_{15}$ substituted or unsubstituted aryl;
k) $C_6$–$C_{22}$ substituted or unsubstituted heterocyclicalkyl;
l) $C_6$–$C_{22}$ substituted or unsubstituted heterocyclicalkenyl;
m) hydroxyl;
n) a carbonyl comprising unit having the formula:

—$(CH_2)_xCOR^7$ wherein $R^7$ is:
  i) —OH;
  ii) —$OR^8$ wherein $R^8$ is hydrogen, $C_1$–$C_{15}$ substituted or unsubstituted linear alkyl, $C_1$–$C_{15}$ substituted or unsubstituted branched alkyl, $C_2$–$C_{22}$ substituted or unsubstituted linear alkenyl, $C_3$–$C_{22}$ substituted or unsubstituted branched alkenyl, or mixtures thereof;
  iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
  iv) $C_1$–$C_{22}$ substituted or unsubstituted linear alkyl;
  v) $C_1$–$C_{22}$ substituted or unsubstituted branched alkyl;
  vi) $C_2$–$C_{22}$ substituted or unsubstituted linear alkenyl;
  vii) $C_3$–$C_{22}$ substituted or unsubstituted branched alkenyl;
  viii) $C_3$–$C_{22}$ substituted or unsubstituted cycloalkyl;
  ix) $C_6$–$C_{22}$ substituted or unsubstituted aryl;
  x) $C_6$–$C_{22}$ substituted or unsubstituted heterocyclicalkyl;
  xi) $C_6$–$C_{22}$ substituted or unsubstituted heterocyclicalkenyl;
  the index x is from 0 to 22;
o) alkyleneoxy units having the formula:

—$(CR^{10}R^{11})_y(CHR^{12}CHR^{13}O)_zR^{14}$ wherein each $R^{10}$, $R^{11}$, and $R^{12}$ is independently;
    i) hydrogen;
    ii) —OH;
    iii) $C_1$–$C_4$ alkyl;
    iv) or mixtures thereof;
  $R^{13}$ is:
    i) hydrogen;
    ii) $C_1$–$C_4$ alkyl;
    iii) or mixtures thereof;
  $R^{14}$ is:
    i) hydrogen;
    ii) $C_1$–$C_4$ alkyl;
    iii) or mixtures thereof;
  $R^{10}$ and $R^{11}$ can be taken together to form a $C_3$–$C_6$ spiroannulated ring, carbonyl unit, or mixtures thereof; y has the value from 0 to 10, z has the value from 1 to 50;
p) any two $R^2$, $R^3$, $R^4$, $R^5$, or $R^6$ units can be taken together to form:
  i) a carbonyl moiety;
  ii) a $C_3$–$C_6$ spiroannulated ring;
  iii) a heterocyclic aromatic ring comprising from 5 to 7 atoms;
  iv) a non-heterocyclic aromatic ring comprising from 5 to 7 atoms;
  v) a heterocyclic ring comprising from 5 to 7 atoms;
  vi) a non-heterocyclic ring comprising from 5 to 7 atoms;
  vii) or mixtures thereof;
q) and mixtures thereof; and
the index n is an integer from 1 to 3; with one or more fragrance raw materials;
b) optionally adding a catalyst; and
c) optionally isolating one or more heterocyclic pro-fragrance as described herein above.

The following are non-limiting examples of heterocyclic pro-fragrances according to the present invention. The pro-fragrances are obtained from single fragrance raw materials, or in the case of pro-fragrance libraries, the pro-fragrances are formed from an admixture of fragrance raw materials.

EXAMPLE 1

Preparation of N-Isopropyl-DL-Serine Methyl Ester (1)

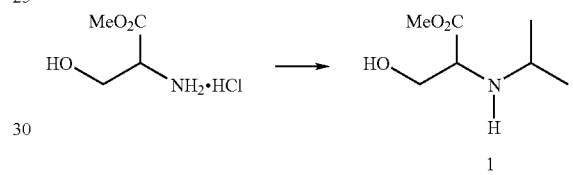

To a slurry of 1 equivalent DL-serine methyl ester hydrochloride and 2 equivalents anhydrous sodium sulfate in methanol is added 1.05 equivalents sodium methoxide. The mixture is stirred at room temperature 5 minutes, after which 3 equivalents of acetone are added and the slurry is stirred overnight. The solids are removed by filtration and the excess acetone is removed from the filtrate under reduced pressure. Once the acetone is removed, platinum (IV) oxide (0.02 equivalents) is added. The slurry is stirred at room temperature 24 hours under a hydrogen atmosphere. The slurry is then filtered and the excess methanol is removed under reduced pressure. The residue is slurried in chloroform and filtered, and the filtrate is washed with dilute sodium bicarbonate, dried over anhydrous sodium sulfate, and filtered. Removal of chloroform under reduced pressure yields the desired product.

EXAMPLE 2

Preparation of Triplal-N-Isopropyl-DL-Serine Methyl Ester Oxazolidine (3)

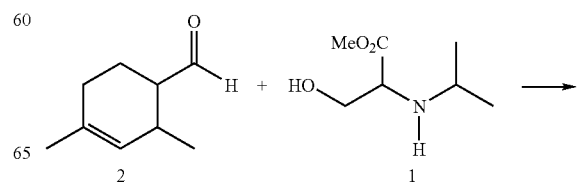

-continued

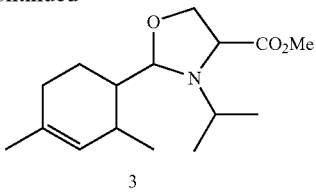

3

A solution of triplal (2, 1.0 equiv), N-isopropyl-DL-serine methyl ester (1, 1.05 equiv) and 2,6-dichlorobenzoic acid (0.01 equiv) is refluxed 6 hours in toluene during which time water is removed by azeotropic distillation. The solution is cooled, washed with saturated sodium bicarbonate, dried over anhydrous sodium sulfate, and filtered. The toluene is subsequently removed under reduced pressure to yield the desired product, 3.

EXAMPLE 3

Preparation of an Oxazolidine Library from an Aldehyde/Ketone Admixture

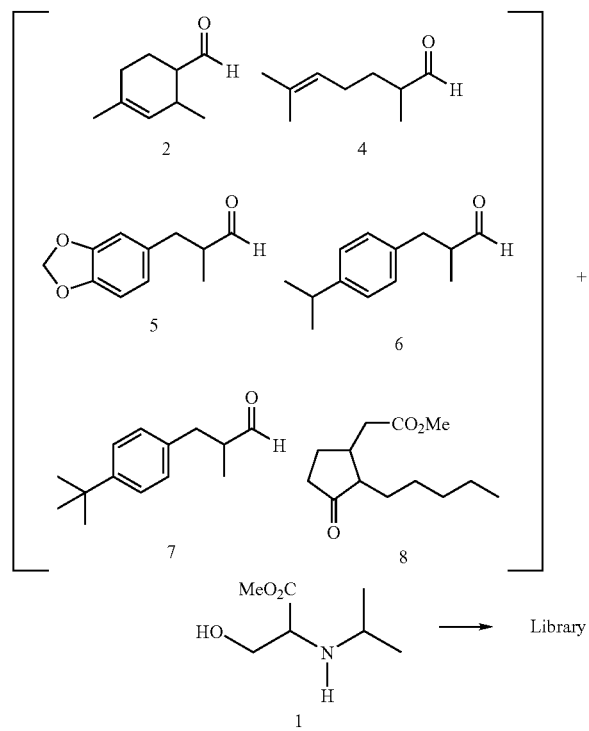

A slurry of 1.0 equiv each of triplal (2), melonal (4), helional (5), pt-bucinal (7), cymal (6) and hedione (8) is stirred for 2 weeks with N-isopropyl-DL-serine methyl ester (1, 6.3 equiv) and anhydrous sodium sulfate (12.0 equiv) at room temperature in anhydrous absolute ethanol. The sodium sulfate is removed by filtration to give the ethanolic solution of products. This solution is used without further purification. Alternatively, the ethanol may be removed under reduced pressure.

What is claimed is:

1. A molecule having formula:

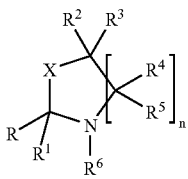

wherein:
A.) X is oxygen or sulfur;
B.) R and $R^1$ are identical to the R and $R^1$ of an aldehyde or ketone having the following fomula:

wherein said aldehyde or ketone is selected from the group consisting of p-methyl phenylacetaldehyde, 2,4-decadienal, 2-octenal, 2-methyldecanal, undec-8-enal, methylnonyl acetaldehyde, 3-(4-t-butylphenyl)-propanal, 3-(4-methoxyphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, 6-nonenal, 2,4-nonadienal, 2,6-nonadienal, 2-methyl decanal, 4-decenal, 9-decenal, 2,6,10-trimethyl-9-undecenal, bourgenonal, citronellyl oxyacetaldehyde, florhydral, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, γ-methyl ionone, α-iso-methyl ionone, α-irone, 6,7-dihydro-1,1,2,3,3-pentamethyl-4(5H)-indanone, cis-jasmone, dihydrojasmone, α-ionone, β-ionone, l-carvone, 2-[2-(4-methyl-3-cyclohexenyl-1-yl)propyl]cyclopentan-2-one, allyl ionone, 1-(2-methyl-5-isopropyl-2-cyclohexenyl)-1-propanone, o-t-butylcyclohexanone, fenchone, α-damascone, β-damascone, δ-damascone, γ-damascone, β-damascenone, and methyl-7,3-dihydro-2H-1,5-benzodioxepine-3-one;

C.) each $R^2$, $R^3$, and each $R^4$ and $R^5$ pair are independently:
   a.) H;
   b.) hydroxyl;
   c.) a carbonyl comprising unit having the formula:

—$(CH^2)_x COR^7$ wherein $R^7$ is:
   (i) —OH;
   (ii) —$OR^8$ wherein $R^8$ is hydrogen, a substituted or unsubstituted, linear or branched moiety selected from the group consisting of $C_1$–$C_{15}$ alkyl, $C_2$–$C_{22}$ alkenyl, or mixtures thereof, wherein said substitution is not halogen;
   (iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;

(iv) a substituted or unsubstituted, linear or branched moiety selected from the group consisting of $C_1$–$C_{22}$ alkyl, $C_2$–$C_{22}$ alkenyl, $C_3$–$C_{22}$ cycloalkyl, (v) a substituted or unsubstituted moiety selected from the group consisting of $C_6$–$C_{22}$ aryl, $C_6$–$C_{22}$ heterocyclicalkyl, $C_6$–$C_{22}$ heterocyclicalkenyl;

the index x is from 1 to 22;

d.) alkyleneoxy units having the formula:

wherein each $R^{10}$, $R^{11}$, and $R^{12}$ is independently hydrogen, —OH, $C_1$–$C_4$ alkyl or mixtures thereof; each $R^{13}$ and $R^{14}$ is independently hydrogen, $C_1$–$C_4$ alkyl or mixtures thereof; $R^{10}$ and $R^{11}$ can be taken together to form a $C_3$–$C_6$ spiroannulated ring, carbonyl unit, or mixtures thereof; y has the value from 0 to 10, z has the value from 1 to 50;

e.) a substituted or unsubstituted, linear or branched moiety selected from the group consisting of $C_1$–$C_{10}$ alkyl, $C_2$–$C_{10}$ alkenyl;

f.) a substituted or unsubstituted moiety selected from the group consisting of $C_3$–$C_{15}$ cycloalkyl, $C_4$–$C_{15}$ cycloalkenyl, $C_6$–$C_{15}$ aryl, $C_6$–$C_{22}$ heterocyclicalkyl, $C_6$–$C_{22}$ heterocyclicalkenyl g.) a substituted or unsubstituted branched moiety selected from the group consisting of $C_4$–$C_{15}$ cycloalkyl, $C_5$–$C_{15}$ cycloalkenyl h.) and mixtures thereof;

D.) $R^6$ is:

a.) $C_1$–$C_{10}$ substituted linear alkyl;

b.) $C_3$–$C_{10}$ substituted branched alkyl;

c.) $C_2$–$C_{10}$ substituted or unsubstituted linear alkenyl;

d.) a substituted or unsubstituted branched moiety selected from the group consisting of $C_3$–$C_{10}$ alkenyl, $C_4$–$C_{15}$ cycloalkyl, $C_5$–$C_{15}$ cycloalkenyl;

e.) a substituted moiety selected from the group consisting of $C_3$–$C_{15}$ cycloalkyl, $C_6$–$C_{15}$ aryl;

f.) a substituted or unsubstituted moiety selected from the group consisting of $C_4$–$C_{15}$ cycloalkyl, $C_6$–$C_{22}$ heterocyclicalkyl, $C_6$–$C_{22}$ heterocyclicalkenyl;

g.) a carbonyl comprising unit having the formula:

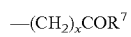

wherein $R^7$ is:

(i) —OH;

(ii) —$OR^8$ wherein $R^8$ is hydrogen, $C_1$–$C_{15}$ substituted linear alkyl, $C_{11}$–$C_{15}$ unsubstituted linear alkyl, $C_1$–$C_{15}$ substituted branched alkyl, $C_{11}$–$C_{15}$ unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen or thioalkyl;

(iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;

(iv) a substituted or unsubstituted, linear or branched moiety selected from the group consisting of $C_1$–$C_{22}$ alkyl, $C_2$–$C_{22}$ alkenyl;

(v) a substituted or unsubstituted moiety selected from the group consisting of $C_3$–$C_{22}$ cycloalkyl, $C_6$–$C_{22}$ aryl, $C_6$–$C_{22}$ heterocyclicalkyl, $C_6$–$C_{22}$ heterocyclicalkenyl;

the index x is from 0 to 22;

h.) alkyleneoxy units having the formula:

wherein each $R^{10}$, $R^{11}$, and $R^{12}$ is independently hydrogen, —OH, $C_1$–$C_4$ alkyl or mixtures thereof; each $R^{13}$ and $R^{14}$ is independently hydrogen, $C_1$–$C_4$ alkyl or mixtures thereof, $R^{10}$ and $R^{11}$ can be taken together to form a $C_3$–$C_6$ spiroannulated ring, carbonyl unit, or mixtures thereof; y has the value from 0 to 10, z has the value from 1 to 50;

i.) and mixtures thereof;

E.) any two $R^2$, $R^3$, $R^4$, $R^5$, or $R^6$ units can be taken together to form:

a.) a carbonyl moiety;

b.) a $C_3$–$C_6$ spiroannulated ring;

c.) a heterocyclic aromatic ring comprising from 5 to 7 atoms;

d.) a non-heterocyclic aromatic ring comprising from 5 to 7 atoms;

e.) a heterocyclic ring comprising from 5 to 7 atoms;

f.) a non-heterocyclic ring comprising from 5 to 7 atoms;

g.) or mixtures thereof; and

F.) the index n is 1 or 2.

2. A molecule according to claim 1 wherein said aldehyde or ketone is selected from the group consisting of 2-octenal, 2-methyldecanal, undec-8-enal, methylnonyl acetaldehyde, 3-(4-t-butylphenyl)-propanal, 3-(4-methoxyphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, 6-nonenal, 2,4-nonadienal, 2,6-nonadienal, 2-methyl decanal, 4-decenal, 9-decenal, 2,6,10-trimethyl-9-undecenal, bourgenonal, citronellyl oxyacetaldehyde, florhydral, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, 6,7-dihydro-1,1,2,3,3-pentamethyl-4(5H)-indanone, cis-jasmone, dihydrojasmone, α-ionone, β-ionone, l-carvone, 2-[2-(4-methyl-3-cyclohexenyl-1-yl)propyl]cyclopentan-2-one, allyl ionone, 1-(2-methyl-5-isopropyl-2-cyclohexenyl)-1-propanone, o-t-butylcyclohexanone, fenchone, α- 2-ethyl-2-heptenal, 2,6-dimethyl-5-heptenal, 3,7-dimethyl-7-hydroxyoctan-1-al, 6-nonenal, 2,4-nonadienal, 2,6-nonadienal, decanal, 2-methyl decanal, 4-decenal, 9-decenal, 2,6,10-trimethyl-9-undecenal, anisaldehyde, bourgenonal, citronellyl oxyacetaldehyde, cyclamen aldehyde, florhydral, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, and p-methylphenoxyacetaldehyde, γ-methyl ionone, α-iso-methyl ionone, methyl β-naphthyl ketone, acetophenone, α-irone, 4-t-pentyl cyclohexanone, 6,7-dihydro-1,1,2,3,3-pentamethyl-4(5H)-indanone, cis-jasmone, dihydrojasmone, α-ionone, β-ionone, dihydro-β-ionone, l-carvone, 2-[2-(4-methyl-3-cyclohexenyl-1-yl)propyl]cyclopentan-2-one, allyl ionone, 1-(2-methyl-5-isopropyl-2-cyclohexenyl)-1-propanone, p-t-butylcyclohexanone, o-t-butylcyclohexanone, ethyl amyl ketone, fenchone, α-damascone, β-damascone, δ-damascone, γ-damascone, β-damascenone, menthone and methyl-7,3-dihydro-2H-1,5-benzodioxepine-3-one;

C.) each $R^2$, $R^3$, and each $R^4$ and $R^5$ pair are independently:
  a.) H;
  b.) hydroxyl;
  c.) a carbonyl comprising unit having the formula:

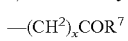

wherein $R^7$ is:
  (i) —OH;
  (ii) —$OR^8$ wherein $R^8$ is hydrogen, a substituted or unsubstituted, linear or branched moiety selected from the group consisting of $C_1$–$C_{15}$ alkyl, $C_2$–$C_{22}$ alkenyl, or mixtures thereof, wherein said substitution is not halogen;
  (iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
  (iv) a substituted or unsubstituted, linear or branched moiety selected from the group consisting of $C_1$–$C_{22}$ alkyl, $C_2$–$C_{22}$ alkenyl, $C_3$–$C_{22}$ cycloalkyl,
  (v) a substituted or unsubstituted moiety selected from the group consisting of $C_6$–$C_{22}$ aryl, $C_6$–$C_{22}$ heterocyclicalkyl, $C_6$–$C_{22}$ heterocyclicalkenyl; damascone, β-damascone, δ-damascone, γ-damascone, β-damascenone, and methyl-7,3-dihydro-2H-1,5-benzodioxepine-3-one.

3. A molecule according to claim 2 wherein said aldehyde or ketone is selected from the group consisting of methylnonyl acetaldehyde, 3-(4-t-butylphenyl)-propanal, 3-(4-methoxyphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, 6-nonenal, 2,4-nonadienal, 2,6-nonadienal, 2-methyl decanal, 4-decenal, 9-decenal, 2,6,10-trimethyl-9-undecenal, bourgenonal, citronellyl oxyacetaldehyde, florhydral, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, α-damascone, β-damascone, δ-damascone, γ-damascone, β-damascenone, and methyl-7,3-dihydro-2H-1,5-benzodioxepine-3-one.

4. A perfume comprising a molecule having the formula:

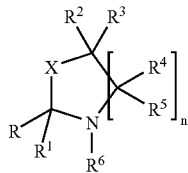

wherein:
A.) X is oxygen or sulfur;
B.) R and $R^1$ are identical to the R and $R^1$ of an aldehyde or ketone having the following fomula:

wherein said aldehyde or ketone is selected from the group consisting of p-methyl phenylacetaldehyde, cis-4-heptenal, 3,7-dimethyloctanal, 2,4-decadienal, tridecanal, tetradecanal, 3-phenylbutanal, 2,4-heptadienal, octanal, 2-octenal, 3,7-dimethyl-2,6-octadien-1-al, 3,7-dimethyl-6-octenal, 2-methyldecanal, undecenal, undec-8-enal, dodecanal, cinnamic aldehyde, heliotropin, vanillin, ethyl vanillin, methylnonyl acetaldehyde, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylpheny)-2,2-dimethylpropanal, 3-methyl-5-phenylpentanal,
the index x is from 1 to 22;
d.) alkyleneoxy units having the formula:

wherein each $R^{10}$, $R^{11}$, and $R^{12}$ is independently hydrogen, —OH, $C_1$–$C_4$ alkyl or mixtures thereof; each $R^{13}$ and $R^{14}$ is independently hydrogen, $C_1$–$C_4$ alkyl or mixtures thereof; $R^{10}$ and $R^{11}$ can be taken together to form a $C_3$–$C_6$ spiroannulated ring, carbonyl unit, or mixtures thereof; y has the value from 0 to 10, z has the value from 1 to 50;
e.) a substituted or unsubstituted, linear or branched moiety selected from the group consisting of $C_1$–$C_{10}$ alkyl, $C_2$–$C_{10}$ alkenyl;
f.) a substituted or unsubstituted moiety selected from the group consisting of $C_3$–$C_{15}$ cycloalkyl, $C_4$–$C_{15}$ cycloalkenyl, $C_6$–$C_{15}$ aryl, $C_6$–$C_{22}$ heterocyclicalkyl, $C_6$–$C_{22}$ heterocyclicalkenyl
g.) a substituted or unsubstituted branched moiety selected from the group consisting of $C_4$–$C_{15}$ cycloalkyl, $C_5$–$C_{15}$ cycloalkenyl
h.) and mixtures thereof;
D.) $R^6$ is:
a.) $C_1$–$C_{10}$ substituted linear alkyl;
b.) $C_3$–$C_{10}$ substituted branched alkyl;
c.) $C_2$–$C_{10}$ substituted or unsubstituted linear alkenyl;
d.) a substituted or unsubstituted branched moiety selected from the group consisting of $C_3$–$C_{10}$ alkenyl, $C_4$–$C_{15}$ cycloalkyl, $C_5$–$C_{15}$ cycloalkenyl;
e.) a substituted moiety selected from the group consisting of $C_3$–$C_{15}$ cycloalkyl, $C_6$–$C_{15}$ aryl;
f.) a substituted or unsubstituted moiety selected from the group consisting of $C_4$–$C_{15}$ cycloalkenyl, $C_6$–$C_{22}$ heterocyclicalkyl, $C_6$–$C_{22}$ heterocyclicalkenyl;
g.) a carbonyl comprising unit having the formula:

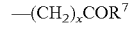

wherein $R^7$ is:
(i) —OH;
(ii) —$OR^8$ wherein $R^8$ is hydrogen, $C_1$–$C_{15}$ substituted linear alkyl, $C_{11}$–$C_{15}$ unsubstituted linear alkyl, $C_1$–$C_{15}$ substituted branched alkyl, $C_{11}$–$C_{15}$ unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen or thioalkyl;
(iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
(iv) a substituted or unsubstituted, linear or branched moiety selected from the group consisting of $C_1$–$C_{22}$ alkyl, $C_2$–$C_{22}$ alkenyl;

(v) a substituted or unsubstituted moiety selected from the group consisting of $C_3$–$C_{22}$ cycloalkyl, $C_6$–$C_{22}$ aryl, $C_6$–$C_{22}$ heterocyclicalkyl, $C_6$–$C_{22}$ heterocyclicalkenyl;
the index x is from 0 to 22;
h.) alkyleneoxy units having the formula:

—$(CR^{10}R^{11})_y(CHR^{12}CHR^{13}O)_zR^{14}$ wherein each $R^{10}$, $R^{11}$, and $R^{12}$ is independently hydrogen, —OH, $C_1$–$C_4$ alkyl or mixtures thereof; each $R^{13}$ and $R^{14}$ is independently hydrogen, $C_1$–$C_4$ alkyl or mixtures thereof, $R^{10}$ and $R^{11}$ can be taken together to form a $C_3$–$C_6$ spiroannulated ring, carbonyl unit, or mixtures thereof; y has the value from 0 to 10, z has the value from 1 to 50;

i.) and mixtures thereof;

E.) any two $R^2$, $R^3$, $R^4$, $R^5$, or $R^6$ units can be taken together to form:
a.) a carbonyl moiety;
b.) a $C_3$–$C_6$ spiroannulated ring;
c.) a heterocyclic aromatic ring comprising from 5 to 7 atoms;
d.) a non-heterocyclic aromatic ring comprising from 5 to 7 atoms;
e.) a heterocyclic ring comprising from 5 to 7 atoms;
f.) a non-heterocyclic ring comprising from 5 to 7 atoms;
g.) or mixtures thereof; and F.) the index n is 1.

5. A perfume according to claim 4 wherein said molecule's R and $R^1$ are identical to the R and $R^1$ of an aldehyde or ketone having the following fomula:

wherein said aldehyde or ketone is selected from the group consisting of 3-phenylbutanal, 2,4-heptadienal, octanal, 2-octenal, 3,7-dimethyl-2,6-octadien-1-al, 3,7-dimethyl-6-octenal, 2-methyldecanal, undecenal, undec-8-enal, dodecanal, cinnamic aldehyde, heliotropin, vanillin, ethyl vanillin, methylnonyl acetaldehyde, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, 6-nonenal, 2,4-nonadienal, 2,6-nonadienal, decanal, 2-methyl decanal, 4-decenal, 9-decenal, 2,6,10-trimethyl-9-undecenal, anisaldehyde, bourgenonal, citronellyl oxyacetaldehyde, cyclamen aldehyde, florhydral, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, and p-methylphenoxyacetaldehyde, 6,7-dihydro-1,1,2,3,3-pentamethyl-4(5H)-indanone, cis-jasmone, dihydrojasmone, α-ionone, β-ionone, dihydro-β-ionone, l-carvone, 2-[2-(4-methyl-3-cyclohexenyl-1-yl) propyl]cyclopentan-2-one, allyl ionone, 1-(2-methyl-5-isopropyl-2-cyclohexenyl)-1-propanone, p-t-butylcyclohexanone, o-t-butylcyclohexanone, ethyl amyl ketone, fenchone, α-damascone, β-damascone, δ-damascone, γ-damascone, β-damascenone, menthone and methyl-7,3-dihydro-2H-1,5-benzodioxepine-3-one.

6. A perfume according to claim 5 wherein said molecule's R and $R^1$ are identical to the R and $R^1$ of an aldehyde or ketone having the following fomula:

wherein said aldehyde or ketone is selected from the group consisting of methylnonyl acetaldehyde, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, 6-nonenal, 2,4-nonadienal, 2,6-nonadienal, decanal, 2-methyl decanal, 4-decenal, 9-decenal, 2,6,10-trimethyl-9-undecenal, anisaldehyde, bourgenonal, citronellyl oxyacetaldehyde, cyclamen aldehyde, florhydral, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, and methylphenoxyacetaldehyde, α-damascone, β-damascone, δ-damascone, γ-damascone, β-damascenone, menthone and methyl-7,3-dihydro-2H-1,5-benzodioxepine-3-one.

7. A perfume comprising a molecule having the formula:

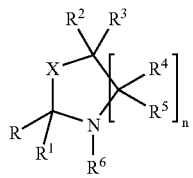

wherein:
A.) X is oxygen or sulfur;
B.) R and $R^1$ are identical to the R and $R^1$ of an aldehyde or ketone having the following fomula:

wherein said aldehyde or ketone is selected from the group consisting of phenylacetaldehyde, p-methyl phenylacetaldehyde, heptanal, cis-4-heptenal, 3,7-dimethyloctanal, 2,4-decadienal, tridecanal, tetradecanal, phenylbutanal, 3-phenyl, 2,4-heptadienal, octanal, 2-octenal, 3,7-dimethyl-2,6-octadien-1-al, 3,7-dimethyl-6-octenal, undecanal, 2-methyldecanal, undecenal, undec-8-enal, dodecanal, cinnamic aldehyde, heliotropin, vanillin, ethyl vanillin, methylnonyl acetaldehyde, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,6,10-trimethyl-9-undecenal, anisaldehyde, bourgenonal, citronellyl oxyacetaldehyde, cyclamen aldehyde, florhydral, benzaldehyde, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, and p-methylphenoxyacetaldehyde, γ-methyl ionone, α-iso-methyl ionone, methyl β-naphthyl ketone, acetophenone, α-irone, 4-t-pentyl cyclohexanone, 6,7-dihydro-1,1,2,3,3-pentamethyl-4(5H)-indanone, cis-jasmone, dihydrojasmone, α-ionone, β-ionone, dihydro-β-ionone, l-carvone, 2-[2-(4-methyl-3-cyclohexenyl-1-yl)propyl]cyclopentan-2-one, allyl ionone, 1-(2-methyl-5-isopropyl-2-cyclohexenyl)-1-propanone, p-t-butylcyclohexanone, o-t-butylcyclohexanone, ethyl amyl ketone, fenchone, α-damascone, β-damascone, δ-damascone, γ-damascone, β-damascenone, menthone and methyl-7,3-dihydro-2H-1,5-benzodioxepine-3-one;

C.) each $R^2$, $R^3$, and each $R^4$ and $R^5$ pair are independently:
  a.) H;
  b.) hydroxyl;
  c.) a carbonyl comprising unit having the formula:

—(CH$_2$)$_x$COR$^7$ wherein $R^7$ is:
    (i) —OH;
    (ii) —OR$^8$ wherein $R^8$ is hydrogen, a substituted or unsubstituted, linear or branched moiety selected from the group consisting of $C_1$–$C_{15}$ alkyl, $C_2$–$C_{22}$ alkenyl, or mixtures thereof, wherein said substitution is not halogen;
    (iii) —N(R$^9$)$_2$ wherein $R^9$ is hydrogen, $C_1$–$C_6$ substituted or unsubstituted linear alkyl, $C_3$–$C_6$ substituted or unsubstituted branched alkyl, or mixtures thereof;
    (iv) a substituted or unsubstituted, linear or branched moiety selected from the group consisting of $C_1$–$C_{22}$ alkyl, $C_2$–$C_{22}$ alkenyl, $C_3$–$C_{22}$ cycloalkyl,
    (v) a substituted or unsubstituted moiety selected from the group consisting of $C_6$–$C_{22}$ aryl, $C_6$–$C_{22}$ heterocyclicalkyl, $C_6$–$C_{22}$ heterocyclicalkenyl;
  the index x is from 1 to 22;
  d.) alkyleneoxy units having the formula:

—(CR$^{10}$R$^{11}$)$_y$(CHR$^{12}$CHR$^{13}$O)$_z$R$^{14}$ wherein each $R^{10}$, $R^{11}$, and $R^{12}$ is independently hydrogen, —OH, $C_1$–$C_4$ alkyl or mixtures thereof; each $R^{13}$ and $R^{14}$ is independently hydrogen, $C_1$–$C_4$ alkyl or mixtures thereof; $R^{10}$ and $R^{11}$ can be taken together to form a $C_3$–$C_6$ spiroannulated ring, carbonyl unit, or mixtures thereof; y has the value from 0 to 10, z has the value from 1 to 50;
  e.) a substituted or unsubstituted, linear or branched moiety selected from the group consisting of $C_1$–$C_{10}$ alkyl, $C_2$–$C_{10}$ alkenyl;
  f.) a substituted or unsubstituted moiety selected from the group consisting of $C_3$–$C_{15}$ cycloalkyl, $C_4$–$C_{15}$ cycloalkenyl, $C_6$–$C_{15}$ aryl, $C_6$–$C_{22}$ heterocyclicalkyl, $C_6$–$C_{22}$ heterocyclicalkenyl
  g.) a substituted or unsubstituted branched moiety selected from the group consisting of $C_4$–$C_{15}$ cycloalkyl, $C_5$–$C_{15}$ cycloalkenyl
  h.) and mixtures thereof;

D.) $R^6$ is:
  a.) $C_1$–$C_{10}$ substituted linear alkyl;
  b.) $C_3$–$C_{10}$ substituted branched alkyl;
  c.) $C_2$–$C_{10}$ substituted or unsubstituted linear alkenyl;
  d.) a substituted or unsubstituted branched moiety selected from the group consisting of $C_3$–$C_{10}$ alkenyl, $C_4$–$C_{15}$ cycloalkyl, $C_5$–$C_{15}$ cycloalkenyl;
  e.) a substituted moiety selected from the group consisting of $C_3$–$C_{15}$ cycloalkyl, $C_6$–$C_{15}$ aryl;
  f.) a substituted or unsubstituted moiety selected from the group consisting of $C_4$–$C_{15}$ cycloalkenyl, $C_6$–$C_{22}$ heterocyclicalkyl, $C_6$–$C_{22}$ heterocyclicalkenyl;
  g.) a carbonyl comprising unit having the formula:

—(CH$_2$)$_x$COR$^7$ wherein $R^7$ is:
    (i) —OH;
    (ii) —OR$^8$ wherein $R^8$ is hydrogen, $C_1$–$C_{15}$ substituted linear alkyl, $C_{11}$–$C_{15}$ unsubstituted linear alkyl, $C_1$–$C_{15}$ substituted branched alkyl, $C_{11}$–$C_{15}$ unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen or thioalkyl;
    (iii) —N(R$^9$)$_2$ wherein $R^9$ is hydrogen, $C_1$–$C_6$ substituted or unsubstituted linear alkyl, $C_3$–$C_6$ substituted or unsubstituted branched alkyl, or mixtures thereof;
    (iv) a substituted or unsubstituted, linear or branched moiety selected from the group consisting of $C_1$–$C_{22}$ alkyl, $C_2$–$C_{22}$ alkenyl;
    (v) a substituted or unsubstituted moiety selected from the group consisting of $C_3$–$C_{22}$ cycloalkyl, $C_6$–$C_{22}$ aryl, $C_6$–$C_{22}$ heterocyclicalkyl, $C_6$–$C_{22}$ heterocyclicalkenyl;
  the index x is from 0 to 22;
  h.) alkyleneoxy units having the formula:

—(CR$^{10}$R$^{11}$)$_y$(CHR$^{12}$CHR$^{13}$O)$_z$R$^{14}$ wherein each $R^{10}$, $R^{11}$, and $R^{12}$ is independently hydrogen, —OH, $C_1$–$C_4$ alkyl or mixtures thereof; each $R^{13}$ and $R^{14}$ is independently hydrogen, $C_1$–$C_4$ alkyl or mixtures thereof; $R^{10}$ and $R^{11}$ can be taken together to form a $C_3$–$C_6$ spiroannulated ring, carbonyl Unit, or mixtures thereof; y has the value from 0 to 10, z has the value from 1 to 50;
  i.) and mixtures thereof;

E.) any two $R^2$, $R^3$, $R^4$, $R^5$, or $R^6$ units can be taken together to form:
  a.) a carbonyl moiety;
  b.) a $C_3$–$C_6$ spiroannulated ring;
  c.) a heterocyclic aromatic ring comprising from 5 to 7 atoms;
  d.) a non-heterocyclic aromatic ring comprising from 5 to 7 atoms;
  e.) a heterocyclic ring comprising from 5 to 7 atoms;
  f.) a non-heterocyclic ring comprising from 5 to 7 atoms;
  g.) or mixtures thereof; and F.) the index n is 2.

8. A perfume according to claim 7 wherein said molecule's R and $R^1$ are identical to the R and $R^1$ of an aldehyde or ketone having the following fomula:

wherein said aldehyde or ketone is selected from the group consisting of phenylbutanal, 3-phenyl, 2,4-heptadienal, octanal, 2-octenal, 3,7-dimethyl-2,6-octadien-1-al, 3,7-dimethyl-6-octenal, 2-methyldecanal, undecenal, undec-8-enal, dodecanal, cinnamic aldehyde, heliotropin, undecenal, ethyl vanillin, methylnonyl acetaldehyde, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,6,10-trimethyl-9-undecenal, anisaldehyde, bourgenonal, citronellyl oxyacetaldehyde, cyclamen aldehyde, florhydral, benzaldehyde, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, and p-methylphenoxyacetaldehyde, 6,7-dihydro-1,1,2,3,3-pentamethyl-4(5H)-indanone, cis-jasmone, dihydrojasmone, α-ionone, β-ionone, dihydro-β-ionone, l-carvone, 2-[2-(4-methyl-3-cyclohexenyl-1-yl)propyl]cyclopentan-2-one, allyl ionone, 1-(2-methyl-5-isopropyl-2-cyclohexenyl)-1-propanone, p-t-butylcyclohexanone, o-t-butylcyclohexanone, ethyl amyl ketone, fenchone, α-damascone, β-damascone, δ-damascone, γ-damascone, β-damascenone, menthone and methyl-7,3-dihydro-2H-1,5-benzodioxepine-3-one.

9. A perfume according to claim 8 wherein said molecule's R and $R^1$ are identical to the R and $R^1$ of an aldehyde or ketone having the following fomula:

wherein said aldehyde or ketone is selected from the group consisting of methylnonyl acetaldehyde, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylpheny)-2,2-dimethylpropanal, 3-methyl-5-phenylpentanal, 2-ethyl-2-heptenal, 2,6-dimethyl-5-heptenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,6,10-trimethyl-9-undecenal, anisaldehyde, bourgenonal, citronellyl oxyacetaldehyde, cyclamen aldehyde, florhydral, benzaldehyde, 3-(4-hydroxy-4-methyl-pentyl)-3-cyclohexene-1-carboxaldehyde, 4-(4-hydroxy-4-methyl-pentyl)-3-cyclohexene-1-carboxaldehyde, 2,4-dimethyl-3-cyclohexene-1-carboxaldehyde, and p-methylphenoxyacetaldehyde, α-damascone, β-damascone, δ-damascone, γ-damascone, β-damascenone, menthone and methyl-7,3-dihydro-2H-1,5-benzodioxepine-3-one.

10. A method for preparing a fragrance delivery system comprises the step of:
A.) combining at least 2 materials from a first group comprising materials having the formula:

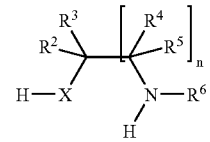

wherein X is oxygen or sulfur; each $R^2$, $R^3$, $R^6$ and each $R^4$ and $R^5$ pair are independently:
a.) hydrogen;
b.) $C_1$–$C_{10}$ substituted or unsubstituted linear alkyl;
c.) $C_3$–$C_{10}$ substituted or unsubstituted branched alkyl;
d.) $C_2$–$C_{10}$ substituted or unsubstituted linear alkenyl;
e.) $C_3$–$C_{10}$ substituted or unsubstituted branched alkenyl;
f.) $C_3$–$C_{15}$ substituted or unsubstituted cycloalkyl;
g.) $C_4$–$C_{15}$ substituted or unsubstituted branched cycloalkyl;
h.) $C_4$–$C_{15}$ substituted or unsubstituted cycloalkenyl;
i.) $C_5$–$C_{15}$ substituted or unsubstituted branched cycloalkenyl;
j.) $C_6$–$C_{15}$ substituted or unsubstituted aryl;
k.) $C_6$–$C_{22}$ substituted or unsubstituted heterocyclicalkyl;
l.) $C_6$–$C_{22}$ substituted or unsubstituted heterocyclicalkenyl;
m.) hydroxyl;
n.) a carbonyl comprising unit having the formula:

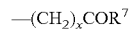

wherein $R^7$ is:
(i) —OH;
(ii) —$OR^8$ wherein $R^8$ is hydrogen, $C_1$–$C_{15}$ substituted or unsubstituted linear alkyl, $C_1$–$C_{15}$ substituted or unsubstituted branched alkyl, $C_2$–$C_{22}$ substituted or unsubstituted linear alkenyl, $C_3$–$C_{22}$ substituted or unsubstituted branched alkenyl, or mixtures thereof;
(iii) —$N(R^9)_2$ wherein $R^9$ is hydrogen, $C_1$–$C_6$ substituted or unsubstituted linear alkyl, $C_3$–$C_6$ substituted or unsubstituted branched alkyl, or mixtures thereof;
(iv) $C_1$–$C_{22}$ substituted or unsubstituted linear alkyl;
(v) $C_1$–$C_{22}$ substituted or unsubstituted branched alkyl;
(vi) $C_2$–$C_{22}$ substituted or unsubstituted linear alkenyl;
(vii) $C_3$–$C_{22}$ substituted or unsubstituted branched alkenyl;
(viii) $C_3$–$C_{22}$ substituted or unsubstituted cycloalkyl;
(ix) $C_6$–$C_{22}$ substituted or unsubstituted aryl;
(x) $C_6$–$C_{22}$ substituted or unsubstituted heterocyclicalkyl;
(xi) $C_6$–$C_{22}$ substituted or unsubstituted heterocyclicalkenyl;
the index x is from 0 to 22;
o.) alkyleneoxy units having the formula:

wherein each $R^{10}$, $R^{11}$, and $R^{12}$ is independently;
  (i) hydrogen;
  (ii) —OH;
  (iii) $C_1$–$C_4$ alkyl;
  (iv) or mixtures thereof;
$R^{13}$ is:
  (i) hydrogen;
  (ii) $C_1$–$C_4$ alkyl;
  (iii) or mixtures thereof;
$R^{14}$ is:
  (i) hydrogen;
  (ii) $C_1$–$C_4$ alkyl;
  (iii) or mixtures thereof;
  $R^{10}$ and $R^{11}$ can be taken together to form a $C_3$–$C_6$ spiroannulated ring, carbonyl unit, or mixtures thereof; y has the value from 0 to 10, z has the value from 1 to 50;
p.) any two $R^2$, $R^3$, $R^4$, $R^5$, or $R^6$ units can be taken together to form:
  (i) a carbonyl moiety;
  (ii) a $C_3$–$C_6$ spiroannulated ring;
  (iii) a heterocyclic aromatic ring comprising from 5 to 7 atoms;
  (iv) a non-heterocyclic aromatic ring comprising from 5 to 7 atoms;
  (v) a heterocyclic ring comprising from 5 to 7 atoms;
  (vi) a non-heterocyclic ring comprising from 5 to 7 atoms;
  (vii) or mixtures thereof;
the index n is an integer from 1 to 3;
with at least 1 material from a second group comprising one or more fragrance raw materials; or combining at least 1 material from said first group with at least 2 materials from said second group,
B.) optionally adding a catalyst; and
C.) optionally isolating one or more heterocyclic pro-fragrances.

\* \* \* \* \*